United States Patent
Pugh et al.

(10) Patent No.: US 10,495,902 B2
(45) Date of Patent: Dec. 3, 2019

(54) SYSTEMS AND METHODS FOR CILIARY MUSCLE VIBRATION DETECTION

(71) Applicant: Johnson & Johnson Vision Care, Inc., Jacksonville, FL (US)

(72) Inventors: Randall B. Pugh, Jacksonville, FL (US); Adam Toner, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

(21) Appl. No.: 15/465,956

(22) Filed: Mar. 22, 2017

(65) Prior Publication Data

US 2018/0275429 A1    Sep. 27, 2018

(51) Int. Cl.
| | | |
|---|---|---|
| G02C 7/08 | (2006.01) | |
| G02C 7/04 | (2006.01) | |
| A61B 3/113 | (2006.01) | |
| A61F 2/16 | (2006.01) | |

(52) U.S. Cl.
CPC .............. *G02C 7/083* (2013.01); *A61B 3/113* (2013.01); *A61F 2/16* (2013.01); *A61F 2/1624* (2013.01); *G02C 7/041* (2013.01); *G02C 7/049* (2013.01); *G02C 7/081* (2013.01)

(58) Field of Classification Search
CPC .. A61F 2/16; A61F 2/1624; A61F 2250/0002; G02C 7/049; G02C 7/04; G02C 7/083; G02C 11/10; A61B 3/113; A61B 5/6821; A61B 5/0488; A61B 5/04888
USPC ............................................. 351/158, 159.03
See application file for complete search history.

(56) References Cited

U.S. PATENT DOCUMENTS

| | | | |
|---|---|---|---|
| 8,834,566 B1 | 9/2014 | Jones | |
| 9,050,185 B2 * | 6/2015 | Pugh | .......................... G02C 7/04 |
| 2006/0122530 A1 * | 6/2006 | Goodall | ............. A61B 5/04001 600/546 |
| 2009/0105817 A1 * | 4/2009 | Bretthauer | ............. A61B 3/113 623/4.1 |
| 2010/0331977 A1 | 12/2010 | Schaper, Jr. | |
| 2013/0184815 A1 * | 7/2013 | Roholt | .................. A61F 2/1635 623/6.22 |
| 2013/0194177 A1 * | 8/2013 | Sakata | ............... H04N 21/4223 345/156 |

(Continued)

FOREIGN PATENT DOCUMENTS

| | | |
|---|---|---|
| EP | 2687898 A1 | 1/2014 |
| WO | WO2015/105881 A1 | 7/2015 |
| WO | WO2015/123616 A1 | 8/2015 |

OTHER PUBLICATIONS

J. Batista, P. Peixoto, H. Araújo, "Visual behaviors for real-time control of a binocular active vision system", Control Engineering Practice, vol. 5, Issue 10, Oct. 1997, pp. 1451-1461 (Year: 1997).*

*Primary Examiner* — William R Alexander

(57) ABSTRACT

The present disclosure relates to sensor systems for electronic ophthalmic devices. In certain embodiments, the sensor systems may comprise a vibration sensor disposed adjacent an eye of a user, the vibration sensor configured to detect a vibration caused at least in part by ciliary muscle movement, the vibration sensor further configured to provide an output and a processor configured to receive the output and to determine a characteristic of the output indicative of the ciliary muscle movement.

32 Claims, 15 Drawing Sheets

(56) References Cited

U.S. PATENT DOCUMENTS

| | | | |
|---|---|---|---|
| 2014/0022505 A1* | 1/2014 | Pugh | A61B 5/6821 351/159.03 |
| 2014/0192318 A1* | 7/2014 | Guth | A61B 3/09 351/205 |
| 2015/0173893 A1* | 6/2015 | Portney | A61F 2/1654 623/5.11 |
| 2016/0030160 A1* | 2/2016 | Markus | A61F 2/1624 623/6.22 |
| 2016/0081793 A1* | 3/2016 | Galstian | G02C 7/04 351/159.03 |
| 2017/0071727 A1* | 3/2017 | Hyde | A61B 5/0031 |
| 2017/0270636 A1* | 9/2017 | Shtukater | G06T 3/20 |
| 2018/0031865 A1* | 2/2018 | Hyde | G02C 7/083 |
| 2018/0098908 A1* | 4/2018 | Chien | A61H 5/00 |

\* cited by examiner

SYSTEMS AND METHODS FOR CILIARY MUSCLE VIBRATION DETECTION

BACKGROUND OF THE DISCLOSURE

1. Field of the Disclosure

The present disclosure relates to electronic ophthalmic devices, such as wearable lenses, including contact lenses, implantable lenses, including intraocular lenses (IDLs) and any other type of device comprising optical components, and more particularly, to sensors and associated hardware and software for detecting ciliary muscle signals in an individual to activate and control electronic ophthalmic devices.

2. Discussion of the Related Art

Ophthalmic devices, such as contact lenses and intraocular lenses, currently are utilized to correct vision defects such as myopia (nearsightedness), hyperopia (farsightedness), presbyopia and astigmatism. However, properly designed lenses incorporating additional components may be utilized to enhance vision as well as to correct vision defects.

Ophthalmic devices may incorporate a lens assembly having an electronically adjustable focus to augment or enhance performance of the eye. The use of embedded electronics in a lens assembly introduces a potential requirement for communication with the electronics, for a method of powering and/or re-energizing the electronics, for interconnecting the electronics, for internal and external sensing and/or monitoring, and for control of the electronics and the overall function of the lens.

Conventional contact lenses are polymeric structures with specific shapes to correct various vision problems as briefly set forth above. To achieve enhanced functionality, various circuits and components have to be integrated into these polymeric structures. For example, control circuits, microprocessors, communication devices, power supplies, sensors, actuators, light-emitting diodes, and miniature antennas may be integrated into contact lenses via custom-built optoelectronic components to not only correct vision, but to enhance vision as well as provide additional functionality.

For example, electronic and/or powered contract lenses may be designed to provide enhanced vision via zoom-in and zoom-out capabilities, or simply modify the refractive capabilities of the lenses. Electronic and/or powered contact lenses may be designed to enhance color and resolution, to display textural information, to translate speech into captions in real time, to offer visual cues from a navigation system, and to provide image processing and internet access. The lenses may be designed to allow the wearer to see in low-light conditions. The properly designed electronics and/or arrangement of electronics on lenses may allow for projecting an image onto the retina, for example, without a variable-focus optic lens, provide novelty image displays and even provide wakeup alerts. Alternately, or in addition to any of these functions or similar functions, the contact lenses may incorporate components for the noninvasive monitoring of the wearer's biomarkers and health indicators.

In addition, because of the complexity of the functionality associated with a powered lens and the high level of interaction between all of its components, there is a need to coordinate and control the overall operation of the electronics and optics.

SUMMARY OF THE DISCLOSURE

The present disclosure relates to powered or electronic ophthalmic devices that comprise an electronic system that, in turn, performs any number of functions, including actuating a variable-focus optic if included. The electronic system may include one or more batteries or other power sources, power management circuitry, one or more sensors, clock generation circuitry, control algorithms, circuitry comprising a vibration (e.g., displacement) sensor, and lens driver circuitry.

The present disclosure relates to electronic ophthalmic devices comprising one or more sensor systems described herein. In certain embodiments, an electronic ophthalmic device may comprise an ophthalmic lens having an optic zone and a peripheral zone. An ophthalmic device may comprise a variable optic element incorporated into the optic zone of the ophthalmic lens, the variable optic being configured to change the refractive power of the ophthalmic lens. An ophthalmic device may comprise an electronic component incorporated into the peripheral zone of the ophthalmic lens, the electronic component including the sensor system for detecting ciliary muscle movement associated with the process of accommodation, the sensor system configured to generate an action for controlling the variable-optic element.

The present disclosure relates to methods for sensing a characteristic of a ciliary muscle in a user of an ophthalmic device. Such a characteristic may be a vibration that is cause to translate through the eye.

The present disclosure relates to a sensing system comprising a vibration sensor disposed adjacent an eye of a user, the vibration sensor configured to detect a vibration caused at least in part by ciliary muscle movement, the vibration sensor further configured to provide an output and a processor configured to receive the output and to determine a characteristic of the output indicative of the ciliary muscle movement.

The present disclosure relates to an ophthalmic device comprising an ophthalmic lens having an optic zone and a peripheral zone, a variable optic element incorporated into the optic zone of the ophthalmic lens, the variable optic being configured to change the refractive power of the wearable ophthalmic lens, and a vibration sensor disposed in the peripheral zone of the ophthalmic lens, the vibration sensor configured to detect a vibration caused at least in part by ciliary muscle movement associated with the process of accommodation, the vibration sensor further configured to provide an output, wherein the variable-optic element is configured to be controlled based at least on the output.

The present disclosure relates to a method for determining a characteristic of the ciliary muscle of a user of an ophthalmic device. Certain methods may comprise receiving, via a vibration sensor disposed adjacent an eye of the user, a vibration signal indicative of a vibration caused at least in part by a change in the characteristic of the ciliary muscle, determining, based at least on the vibration signal, a displacement signature indicative of the characteristic of the ciliary muscle, and implementing, via a control, a predetermined function associated with the ophthalmic device.

BRIEF DESCRIPTION OF THE DRAWINGS

The foregoing and other features and advantages of the disclosure will be apparent from the following, more particular description of preferred embodiments of the disclosure, as illustrated in the accompanying drawings.

DETAILED DESCRIPTION OF THE PREFERRED EMBODIMENTS

Figure 1:
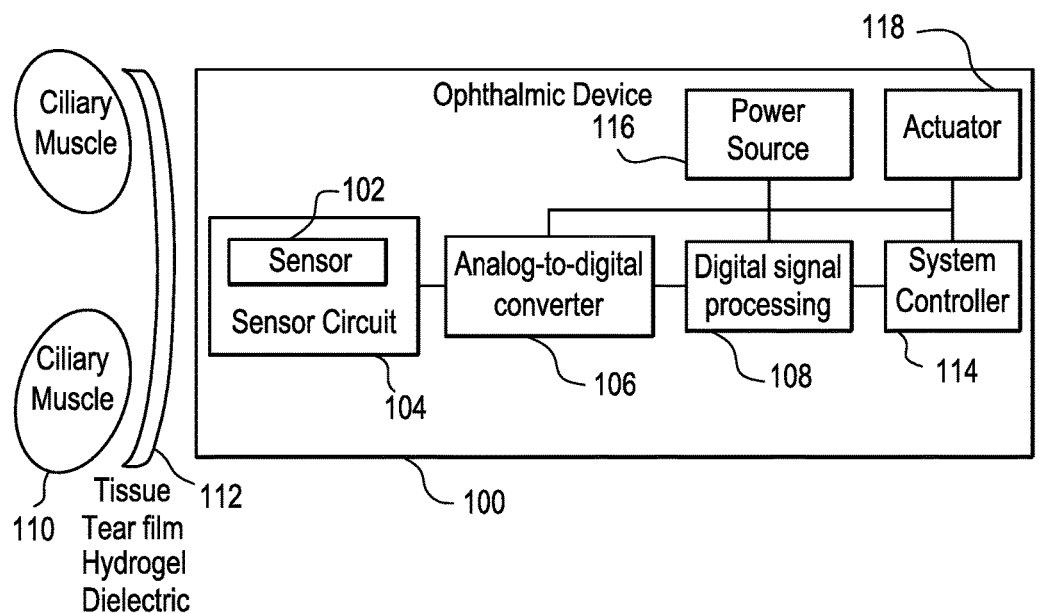
FIG. 1 illustrates an exemplary ophthalmic device comprising a sensor system in accordance with some embodiments of the present disclosure.

Ophthalmic devices may include implantable device and/or wearable devices, such as contact lenses. Conventional contact lenses are polymeric structures with specific shapes to correct various vision problems as briefly set forth above. To achieve enhanced functionality, various circuits and components may be integrated into these polymeric structures. For example, control circuits, microprocessors, communication devices, power supplies, sensors, actuators, light-emitting diodes, and miniature antennas may be integrated into contact lenses via custom-built optoelectronic components to not only correct vision, but to enhance vision as well as provide additional functionality as is explained herein.

Electronic and/or powered ophthalmic devices such as contact lenses may be designed to provide enhanced vision via zoom-in and zoom-out capabilities, and/or to modify the refractive capabilities of the lenses. Electronic and/or powered devices may be designed to enhance color and resolution, to display textural information, to translate speech into captions in real time, to offer visual cues from a navigation system, and to provide image processing and internet access. The devices may be designed to allow the user/wearer to see in low light conditions. The properly designed electronics and/or arrangement of electronics on devices (e.g., lenses) may allow for projecting an image onto the retina, for example, without a variable focus optic lens, provide novelty image displays and even provide wakeup alerts. Alternately, or in addition to any of these functions or similar functions, the ophthalmic devices (e.g., contact lenses) may incorporate components for the noninvasive monitoring of the wearer's biomarkers and health indicators. For example, sensors built into the ophthalmic devices (e.g., contact lenses) may allow a diabetic patient to keep tabs on blood sugar levels by analyzing components of the tear film without the need for drawing blood. In addition, an appropriately configured lens may incorporate sensors for monitoring cholesterol, sodium, and potassium levels, as well as other biological markers. This coupled with a wireless data transmitter could allow a physician to have almost immediate access to a patient's blood chemistry without the need for the patient to waste time getting to a laboratory and having blood drawn. In addition, sensors built into the ophthalmic devices (e.g., contact lenses) may be utilized to detect light incident on the eye to compensate for ambient light conditions or for use in determining blink patterns.

The powered or electronic ophthalmic devices of the present disclosure may comprise the necessary elements to correct and/or enhance the vision of patients with one or more of the above described vision defects or otherwise perform a useful ophthalmic function. In addition, the electronic contact lens may be utilized simply to enhance normal vision or provide a wide variety of functionality as described above. The electronic contact lens may comprise a variable focus optic lens, an assembled front optic embedded into a contact lens or just simply embedding electronics without a lens for any suitable functionality. The electronic lens of the present disclosure may be incorporated into any number of contact lenses as described above. In addition, intraocular lenses may also incorporate the various components and functionality described herein. However, for ease of explanation, the disclosure will focus on an electronic contact lens to correct vision defects intended for single-use daily disposability.

The present disclosure may be employed in a powered ophthalmic device comprising an electronic system, which actuates a variable-focus optic or any other device or devices configured to implement any number of numerous functions that may be performed. The electronic system includes one or more batteries or other power sources, power management circuitry, one or more sensors, clock generation circuitry, control algorithms and circuitry, and lens driver circuitry. The complexity of these components may vary depending on the required or desired functionality of the lens.

Control of an electronic or a powered ophthalmic lens may be accomplished through a manually operated external device that communicates with the lens, such as a hand-held remote unit. For example, a fob may wirelessly communicate with the powered lens based upon manual input from the wearer. Alternately, control of the powered ophthalmic lens may be accomplished via feedback or control signals directly from the wearer. For example, sensors built into the lens may sense signals indicative of ciliary muscle movement, i.e. contraction and relaxation, to compensate for crystalline lens dysfunction or any other problems associated with visual acuity or eye disease. Based upon these signals, the powered ophthalmic lens may change state, for example, its refractive power, in order to either focus on a near object or a distant object.

The systems, devices, and methods of the present disclosure may be configured to sense movement of the ciliary muscle of a user, for example, using vibration sensing. The ciliary muscle in the eye is the structure that controls or attempts to control the shape of the crystalline lens. The crystalline lens is encased in the capsule which is suspended by zonules connected to the ciliary muscle. The ciliary muscle causes the zonules to contract or to relax thereby changing the shape and/or focusing power of the crystalline lens. If the crystalline is unable to partially or fully respond to ciliary muscle movement, the individual will be unable to accommodate, a disease state known as presbyopia. Therefore, a powered or electronic ophthalmic lens that responds to these same signals may be utilized to compensate for this loss of ability to accommodate.

Each eye contains a ciliary muscle, which is located around or proximate to the crystalline lens. Zonules attach to the ciliary muscle and, additionally, attach to the crystalline lens. The ciliary muscle controls accommodation for viewing objects at varying distances by changing the shape of the crystalline lens. For example, when focusing on a nearby object where a short focal distance is needed, the ciliary muscle contracts and slackens the zonules causing the crystalline lens to become rounder and more compressed.

As an example, when focusing on a distant object and a lengthened focal distance is needed, the ciliary muscle relaxes and the zonules pull on the edges of the crystalline lens causing it to be thinner and flatter. Accordingly, electrical signals derived from the changes in characteristics of the ciliary muscle may be utilized as a way to activate and control a powered ophthalmic device. As an example, when the ciliary muscle constricts and relaxes, the movement of the ciliary muscle and associated structures, such as the zonules, cause a change in impedance to current flowing through those structures, for example by altering the degree to which muscle fibers are oriented parallel/perpendicular to the flow of electrical current and hence changing the electrical impedance. This impedance and change in impedance may be indicative of a ciliary muscle characteristic such as a configuration of the muscle fibers. As a further example, when the ciliary muscle constricts and relaxes, the movement of the ciliary muscle and associated structures, such as the zonules, may cause a vibration that may translate through the eye. As such, vibration sensors (e.g., displacement sensors, tactile sensors, etc.) may be configured to detect a vibration in the eye.

Powered or electronic ophthalmic devices may have to account for the various ciliary muscle signals detected from an individual utilizing the powered or electronic ophthalmic devices. More specifically, powered ophthalmic devices may need to detect and differentiate between various ciliary muscle signals (e.g., vibrations), and from one or more of other signals, noise, and interference.

The iris, or colored part of the eye, is the partition between the anterior and posterior chambers of the eye and it is made up of two muscles that regulate the size of the pupil to control the amount of light entering the eye. The dilator muscle opens the pupil and the sphincter muscle closes the pupil. The eye also has six extraoccular muscles that control the overall movement of the eye or eye globe. The sensing of the extraoccular muscles and/or the dilator and sphincter muscles may provide other or additional functionality for a powered or electronic ophthalmic lens. The eye comprises a number of liquid components, including the tear film. These liquids are excellent conductors of electrical signals as well as other signals, such as acoustic signals or sound waves. Accordingly, it should be understood that a neuromuscular sensor in accordance with the present disclosure may provide feedback signals for controlling any number of functions that may be implemented by a powered or electronic ophthalmic lens. However, in accordance with the present disclosure, the circuitry is configured to detect, isolate and amplify ciliary muscle signals while filtering out noise and other muscle signals.

A sensor, the components of which may be embedded in a powered contact lens, may detect characteristics of different eye muscle signals. For example, various signals may include one or more of when an eye is moving up or down, focusing up close, and adjusting to a change in ambient light levels, such as from light to dark, dark to light or any other light condition. The ciliary muscle controls the shape of the crystalline lens in order to focus on a near or distant object. The sensor relies on tracking various signals, including amplitude, time-domain response and frequency composition, produced by or emitted from the ciliary muscle in certain sample conditions, such as when an individual is reading, focusing far away, or in a room with fluorescent lighting. It is important to note that this list of conditions is exemplary and not exhaustive.

These ciliary muscle signal samples may be logged and tracked wherein the various waveforms and frequencies of each of the signals may be distinguished from one or more of other signals, noise, and interference. As set forth above, the circuitry of the present disclosure is preferably designed to detect, isolate and/or filter ciliary muscle signals. In alternate embodiments, other muscle signals may be utilized for augmenting or implementing other ocular functions. Whenever the sensor detects a recognized ciliary muscle signal, it may trigger activity in the electronic circuitry, for example, activating an electronic lens.

As set forth herein, the crystalline lens of the eye is suspended by zonules, the fibers that are attached to both the crystalline lens and the ciliary muscle. The ciliary muscle reacts to various stimuli and sends out any number of signals that are normally interpreted by the central nervous system whereupon some action takes place. For example, in accommodation, when the retina receives an image from a close or near object, the ciliary muscle contracts. This contraction causes the zonules to relax and allows the crystalline lens to thicken which in turn makes the lens stronger (adding plus power) which is needed to focus on a close up or near object. This process is known as accommodation. More specifically, this is one of the more widely accepted theories of how the ciliary muscle works in conjunction with the zonules and the crystalline lens in accommodation. In individuals with presbyopia, the crystalline lens becomes less flexible, and thus may not move regardless of the ciliary muscle contraction. Even though the crystalline lens does not respond, the ciliary muscle still contracts or otherwise reacts and sends out a measurable signal and this measurable signal may be utilized with a powered lens to compensate for the lack of response by the crystalline lens. In other words, regardless of the theory of how the precise mechanism of accommodation works relative to the ciliary muscle, the ciliary muscle does react to different stimuli and thus its response may be measured with the right sensors. Accordingly, a complete set of ciliary muscle responses may be measured under various conditions or stimuli and a set of data developed to be utilized as a set of feedback signals for controlling a powered or electronic ophthalmic lens directly. The powered or electronic ophthalmic lens may be utilized to compensate for various visual acuity problems, including presbyopia, as well as any number of other conditions.

There may be various methods used to implement some exemplary embodiments of the present disclosure. For example, sensors may detect a ciliary muscle signal utilizing displacement (e.g., vibration) sensing and/or a microphone, alone or in combination with, one or more of electromyography (EMG), magnetomyography (MMG), phonomyography (PMG), and impedance. Furthermore, sensors may comprise a non-contact sensor, such as an antenna that is embedded into a contact lens, but that does not directly touch the surface of an eye. Alternately, sensors may comprise a contact sensor, such as contact pads that directly touch the surface of an eye. It is important to note that any number of suitable devices and processes may be utilized for the detection of signals from the ciliary muscle as is explained in detail subsequently. As described herein, any type of sensor and/or sensing technology may be utilized.

In certain embodiments, ophthalmic devices may comprise an ophthalmic lens having an optic zone and a peripheral zone. Ophthalmic devices may comprise a variable optic element incorporated into the optic zone of the ophthalmic lens, the variable optic being configured to change the refractive power of the wearable ophthalmic lens. Ophthalmic devices may comprise a vibration sensor disposed in the peripheral zone of the ophthalmic lens, the vibration sensor configured to detect a vibration caused at least in part by ciliary muscle movement associated with the process of accommodation, the vibration sensor further configured to provide an output, wherein the variable-optic element is configured to be controlled based at least on the output.

FIG. 1 illustrates, in block diagram form, an ophthalmic device 100 disposed on the front surface of the eye or cornea 112, in accordance with one exemplary embodiment of the present disclosure. Although the ophthalmic device 100 is shown and described as a being disposed on the front surface of the eye, it is understood that other configurations, such as those including intraocular lens configuration may be used. In this exemplary embodiment, the sensor system may comprise one or more of a sensor 102, a sensor circuit 104, an analog-to-digital converter 106, a digital signal processor 108, a power source 116, an actuator 118, and a system controller 114. As illustrated, the ciliary muscle 110 is located behind the front eye surface or cornea 112. More specifically, the globe of the eye can be divided into two segments; namely, the anterior chamber and the posterior chamber. The iris is the partition between the anterior and posterior chambers. Between the front surface of the crystalline lens and the back surface of the iris is the posterior chamber. At the base of the iris is the ciliary body which produces aqueous humor and is continuous with the ciliary muscle. The ophthalmic device 100 is placed onto the front surface of the eye 112 wherein the electronic circuitry of the sensor system may be utilized to implement the neuromuscular sensing of the present disclosure. The sensor 102 as well as the other circuitry is configured to sense signals from ciliary muscle 110 actions through the various tissue and liquids forming the eye and produced by the eye. As set forth above, the various fluids comprising the eye are good conductors of electrical and acoustical signals.

In this exemplary embodiment, the sensor 102 may be at least partially embedded into the ophthalmic device 100. The sensor 102 may be in mechanical communication with the eye, for example disposed to sense vibration associated with (e.g., translating through) the eye. The sensor 102 may be or comprise one or more components configured to sense a displacement (e.g., vibration) at or near the eye. The sensor 102 may comprise a micro ball sensor, a piezo vibration sensor, a cantilever sensor, a microphone, and the like. The sensor 102 may comprise a piezoelectric, sonic, subsonic, and/or ultrasonic sensor component. The sensor 102 may comprise an emitter/detector pair. The sensor 102 may be configured to generate an electrical signal indicative of the sensed vibration. As such, when characteristics of the ciliary muscle change, the sensor 102 may sense displacement(s) due to such change and may generate the electrical signal indicative of such change or resultant characteristic. For example, there may be various signals detected by the sensor 102 depending on the state that a ciliary muscle is in, such as whether it is contracting or relaxing, or on the type of action that a ciliary muscle is trying to perform, such as causing the eye to focus on a near object or a far object. As a further example, particular states of the ciliary muscle representing one or more characteristics of the ciliary muscle at a given time, may be associated with a particular displacement signature indicative of the particular state. Additionally or alternatively, the change between states of the ciliary muscle may be associated with a particular displacement signature indicative of the particular transition between states. A set of displacement signatures may be determined (e.g., via experimentation) and may be stored for subsequent comparison. The set of displacement signatures may be generated using machine learning, heuristics, signal processing, and/or comparison to one or more predetermined signatures. The set of displacement signatures may be user specific and/or time specific based on actual or predictive use patterns over a period of time.

Figure 3:
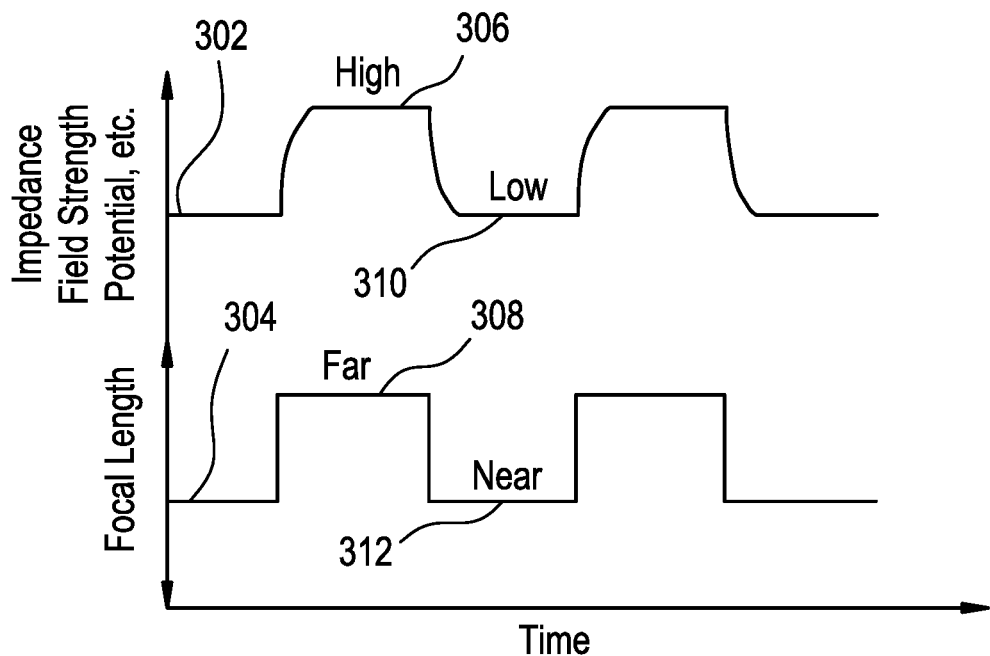
FIG. 3 is a graphical representation demonstrating correlations between measurable electrical parameters and the eye's desired focal length in accordance with the present disclosure.
Figure 19:
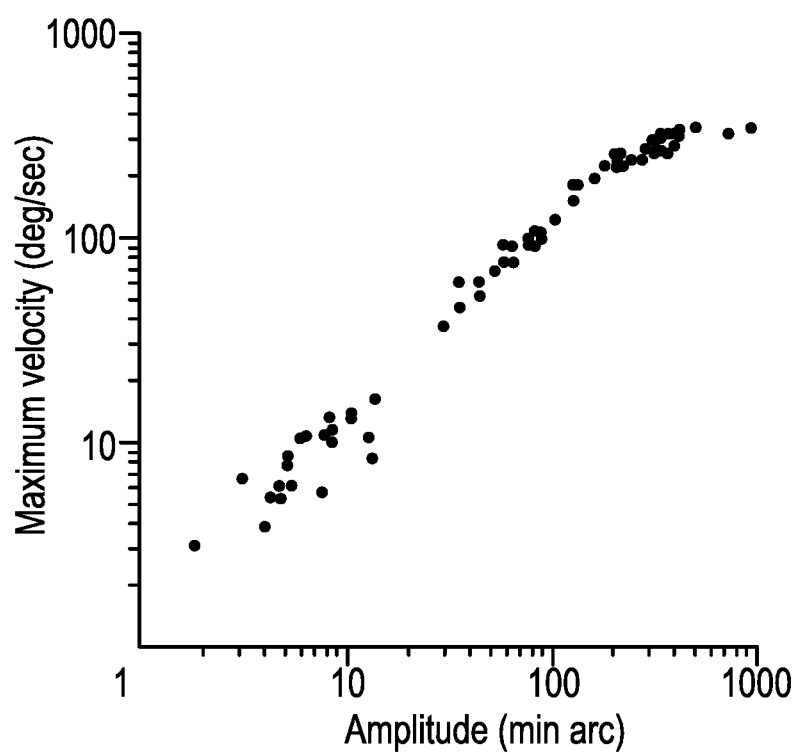
FIG. 19 is a prior art plot of maximum velocities of saccades and microsaccades of relative to amplitudes, from Zuber B L, Stark L., Cook G: *Science* 150:1459, 1965.
Figure 20:
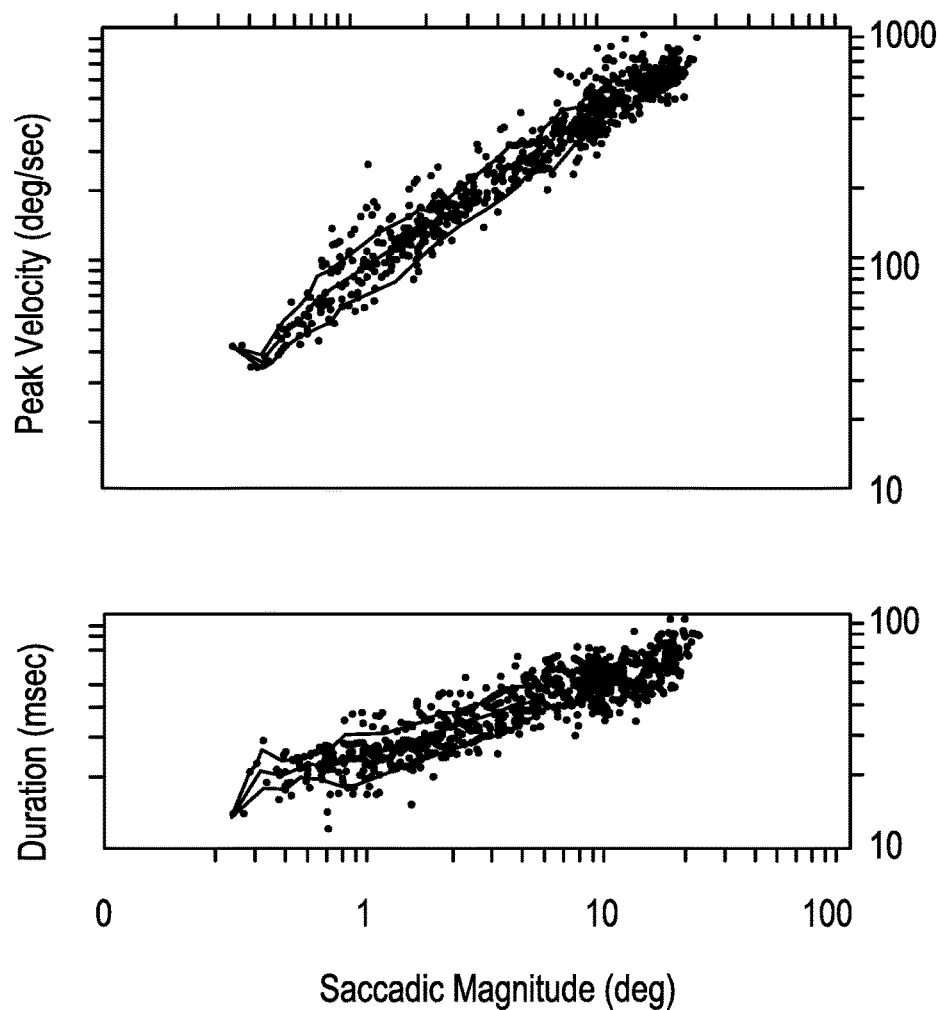
FIG. 20 illustrates prior art main-sequence diagrams showing peak velocity, duration, and the first peak acceleration as a function of saccadiac magnitude for the saccadic eye movement of 13 individuals with normal vision, from Bahill A T, Brockenbrough A, Troost T: *Invest Ophthalmol Vis Sci* 21:116, 1981.
Figure 21:
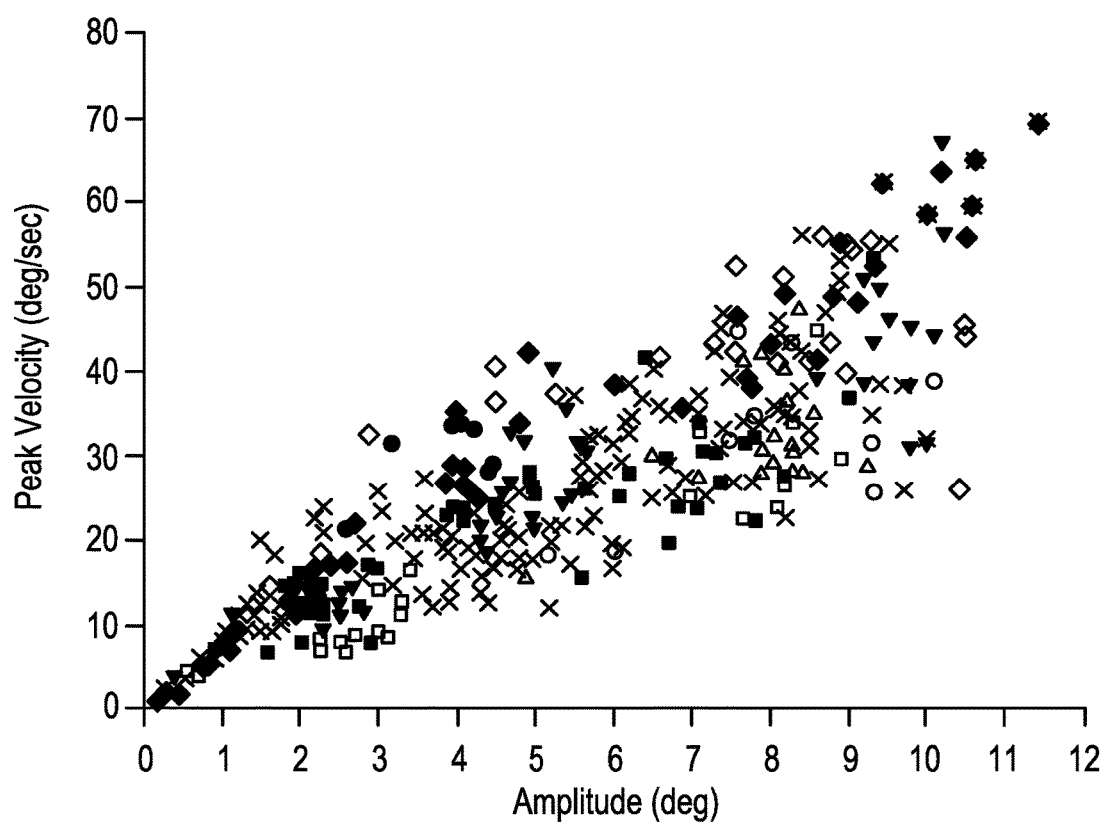
FIG. 21 is a prior art plot of main sequence disparity vergence responses for a variety of stimulus conditions in one subject, from Hung G K, Ciuffreda K J, Semmlow J L, Horng J L: *Invest Ophthalmol Vis Sci* 35:3486, 1994.

Example signatures include those associated with the ciliary muscle contracting and relaxing in response to an accommodative stimulus to change lens focus. Peak intensity of muscle movement may occur when the stimulus changes near/far or far/near, which may be represented by a derivative of the signals 302, 306 (FIG. 3). This muscle movement causes a corresponding change in tension and movement of the zonules and lens. A characteristic signal associated with such ciliary muscle movement, translated through the zonules and eye to an appropriate sensor, may have distinctly different characteristics in amplitude, duration, and frequency than other signals around the eye. For example, natural accommodation occurs over a period of hundreds of milliseconds and involves both fast changes in reaction to stimulus change and slow changes to maintain focus as part of a feedback loop. Signal processing can differentiate between the fast changes, slow changes, and other signals such as eye movements. As an example, data captured via one or more sensors and/or sensor systems of the present disclosure may be processed based on comparative data such as maximum velocities of saccades and microsaccades of relative to amplitudes (FIG. 19), main-sequence diagrams showing peak velocity, duration, and the first peak acceleration as a function of saccadiac magnitude for the saccadic eye movement (FIG. 20), and/or main sequence disparity vergence responses (FIG. 21), for example. Such processing (e.g., comparison, filtering, etc.) may facilitate the differentiation of noise and may be used to differentiate between the fast changes, slow changes, and other signals such as eye movements Other comparative data may be collected and used to process the information captured via the sensors and sensor systems of the present disclosure.

Returning to FIG. 1, the sensor circuit 104 or sensor system may be configured to process signals received by the sensor 102. As an example, the sensor circuit 104 may be configured to amplify a signal to facilitate integration of small changes in signal level. As a further example, the sensor circuit 104 may be configured to amplify a signal to a useable level for the remainder of the system, such as giving a signal enough power to be acquired by various components of the sensor circuit 104 and/or the analog-to-digital converter 106. In addition to providing gain, the sensor circuit 104 may include other analog signal conditioning circuitry such as filtering and impedance matching circuitry appropriate to the sensor 102 and sensor circuit 104 output. The sensor circuit 104 may comprise any suitable device for amplifying and conditioning the signal output by the sensor 102. For example, the sensor circuit 104 may simply comprise a single operational amplifier or a more complicated circuit comprising one or more operational amplifiers.

As set forth above, the sensor 102 and the sensor circuit 104 are configured to capture and isolate the signals indicative of characteristic of the ciliary muscle from the noise and other signals produced in or by the eye and convert it to a signal usable ultimately by the system controller 114. The system controller 114 is preferably preprogrammed to recognize the various signals produced by the ciliary muscle under various conditions and provide an appropriate output signal to the actuator 118.

In this exemplary embodiment, the analog-to-digital converter 106 may be used to convert an analog signal output from the amplifier into a digital signal for processing. For example, the analog-to-digital converter 106 may convert an analog signal output from the sensor circuit 104 into a digital signal that may be useable by subsequent or downstream circuits, such as a digital signal processing system 108 or microprocessor. A digital signal processing system or digital signal processor 108 may be utilized for digital signal processing, including one or more of filtering, processing, detecting, and otherwise manipulating/processing sampled data to discern a ciliary muscle signal from noise and interference. The digital signal processor 108 may be preprogrammed with the ciliary muscle responses described above. The digital signal processor 108 may be implemented utilizing analog circuitry, digital circuitry, software and/or preferably a combination thereof. For example, various ciliary muscle signals that may occur within a certain frequency range may be distinguishable from other signals, noise, and interference that occur within other frequency ranges. Certain commonly occurring noise and interference signals may be notched at various stages in the signal acquisition chain utilizing analog or digital filters, for example, harmonics of 50/60 Hz AC mains and fluorescent lights. It may be advantageous to filter various noise and interference signals through a combination of analog and digital signal processing, for example to use differential circuit design techniques to reject common-mode noise that could overload a sensitive amplifier, while performing time- and frequency-domain analysis (e.g. to differentiate ciliary muscle signals from eye movements) in digital signal processing.

A power source 116 supplies power for numerous components comprising the non-contact sensor system. The power may be supplied from a battery, energy harvester, or other suitable means as is known to one of ordinary skill in the art. Essentially, any type of power source may be utilized to provide reliable power for all other components of the system. A ciliary muscle signal, processed from analog to digital, may enable activation of the system controller 114. Furthermore, the system controller 114 may control other aspects of a powered contact lens depending on input from the digital signal processor 108, for example, changing the focus or refractive power of an electronically controlled lens through an actuator 118.

In further alternate exemplary embodiments, the system controller 114 may receive input from sources including one or more of a contact sensor, a blink detector, and a fob control. By way of generalization, it may be obvious to one skilled in the art that the method of activating and/or controlling the system controller 114 may require the use of one or more activation methods. For example, an electronic or powered contact lens may be programmable specific to an individual user, such as programming a lens to recognize both of an individual's ciliary muscle signals when performing various actions, for example, focusing on an object far away, or focusing on an object that is near, and an individual's blink patterns. In some exemplary embodiments, using more than one method to activate an electronic contact lens, such as ciliary muscle signal detection and blink detection, may give the ability for each method to crosscheck with another before activation of the contact lens occurs. An advantage of crosschecking may include mitigation of false positives, such as minimizing the chance of unintentionally triggering a lens to activate.

In one exemplary embodiment, the crosschecking may involve a voting scheme, wherein a certain number of conditions are met prior to any action taking place. The actuator 118 may comprise any suitable device for implementing a specific action based upon a received command signal. The actuator 118 may comprise an electrical device, a mechanical device, a magnetic device or any combination thereof. The actuator 118 receives a signal from the system controller 114 in addition to power from the power source 116 and produces some action based on the signal from the system controller 114. For example, if the system controller 114 signal is indicative of the wearer trying to focus on a near object, the actuator 118 may be utilized to somehow change the refractive power of the electronic ophthalmic lens.

Figure 2:
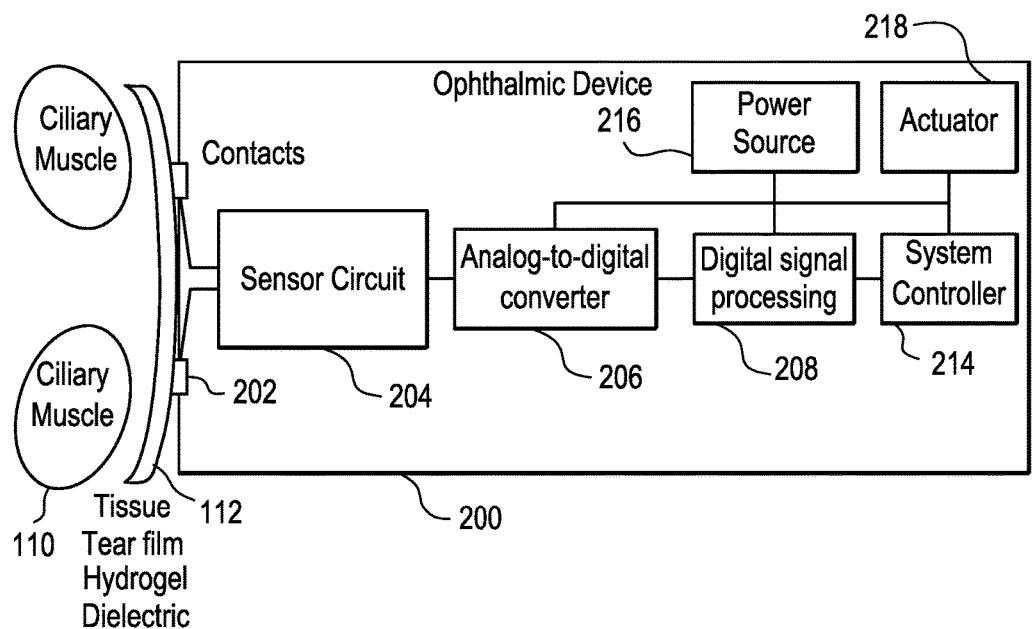
FIG. 2 illustrates an exemplary ophthalmic device comprising a sensor system in accordance with some embodiments of the present disclosure.

FIG. 2 illustrates an ophthalmic device 200, comprising a sensor system, shown on the front surface of the eye or cornea 112 in accordance with another exemplary embodiment of the present disclosure. In this exemplary embodiment, a sensor system may comprise a contact or multiple contacts 202, a sensor circuit 204, an analog-to-digital converter 206, a digital signal processor 208, a power source 216, an actuator 218, and a system controller 214. The ciliary muscle 110 is located behind the front eye surface or cornea 112. The ophthalmic device 200 is placed onto the front surface of the eye 112, such that the electronic circuitry of the sensor may be utilized to implement the neuromuscular sensing of the present disclosure. The components of this exemplary system are similar to and perform the same functions as those illustrated in FIG. 1, with the exception of contacts 202 and the sensor circuit 204. In other words, since direct contacts 202 are utilized, there is no need for an antenna or an amplifier to amplify and condition the signal received by the antenna.

In the illustrated exemplary embodiment, the contacts 202 may provide for a direct electrical connection to the tear film and the eye surface. For example, the contacts 202 may be implemented as metal contacts that are exposed on the back curve of the ophthalmic device 200 and be made of biocompatible conductive materials, such as gold or titanium. Furthermore, the contact lens polymer may be molded around the contacts 202, which may aid in comfort on the eye and provide improved conductivity through the ophthalmic device 200. Additionally, the contacts 202 may provide for a low resistance connection between the eye's surface 112 and the electronic circuitry within the ophthalmic device 200. Four-terminal sensing, also known as Kelvin sensing, may be utilized to mitigate contact resistance effects on the eye. The sensor circuit 204 may emit a signal with several constituent frequencies or a frequency sweep, while measuring the voltage/current across the contacts 202.

In an alternate exemplary embodiment, the sensor circuit 204 may be configured to sense a vibration produced by the contraction or relaxation of the ciliary muscle 110. It is important to note that various types of sensors may be utilized, given that the eye comprises various fluids, including tears which are excellent conductors. The sensor circuit 204 may be configured to measure vibration, wherein the vibration may change based upon what a ciliary muscle is trying to do, such as contracting or relaxing. In this exemplary embodiment, the analog-to-digital converter 206 and the digital signal processing 208 may be configured differently for a contact-based sensor as opposed to a non-contact based sensor, as described in FIG. 1. For example, there may be a different sample rate, a different resolution, and different signal processing algorithm 208.

FIG. 3 illustrates a graph demonstrating correlations between measurable electrical parameters and the eye's focal length as described in the referenced literature. Trace 302 is a representation of an electrically measurable signal in or on the eye. For example, such signals may be detected as one or more of impedance, voltage potential, induced electromagnetic field, and other measurable parameters (e.g., displacement). Trace 304 is a representation of a desired focal length wherein for example, if clinical subjects focused on objects at 0.2 and 2.0 meter distances, the ciliary muscle may undergo a corresponding change in measurable electrical parameters and displacement characteristics accordingly, depending on the distance of focus. However, using the same example, the actual focal length of a lens may not change or only changes minimally, such as in cases where a person may be presbyopic and the lens of the eye is too rigid and unable to accommodate for a change in focus, even where the ciliary muscles are responding to the change.

As described in the literature, there is a correlation between a measurable electrical signal and a focal length. As illustrated in FIG. 3, impedance is high 306 when the focal length is far 308 and impedance is low 310 when the focal length is near 312. Additionally, as described in the literature but not illustrated in FIG. 3, a correlation exists between the amplitude of traces 302 and 304 for intermediate values. Moreover, displacement signatures may be associated (e.g., correlated) with a particular state of the ciliary muscle and/or transitions between such states, which may also be associated with an impedance and/or change in such impedance.

In some exemplary embodiments, characteristics of an electrical signal (e.g., trace 302, 304) such as shape, frequency content, timing, and amplitude, may vary due to several factors including one or more of a detection method utilized (e.g., vibration, impedance, or field strength), an individual's eye physiology, ciliary muscle fatigue, electrolyte levels in the eye, state of presbyopia, interference, and focal length. For example, depending on the type of detection method used, the correlation between desired focus and measurable electrical parameter may have the opposite polarity from what is illustrated in FIG. 3.

Additionally, for example, a signal may be distorted from carrying one or more of significant noise, interference from other muscles, and interference from various environmental sources or due to the effects of aging, disease or genetics. Accordingly, studies of eye response and individual user measurement and training may be used to program the digital signal circuitry to properly detect the eye's desired focal length. Parameters of the digital signal processing may be adjusted in response to other measurements, for example, time of day, measured electrolyte levels, ambient light levels and the like. Furthermore, recorded samples of a user's eye focus signals may be used in conjunction with interference detection and mitigation techniques. It is important to note that any type of sensor may be utilized in accordance with the present disclosure. As long as there is muscle movement associated with changing conditions, it may be sensed, processed and utilized to enhance, augment or simply provide vision correction.

Figure 4:
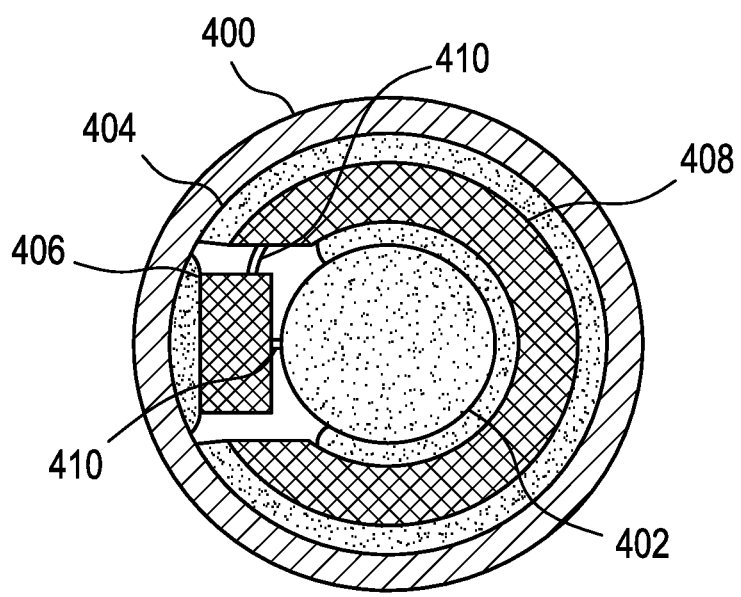
FIG. 4 is a planar view of an ophthalmic device comprising electronic components, including a sensor system and a variable-optic element in accordance with the present disclosure.

Referring now to FIG. 4, there is illustrated, in planar view, a wearable electronic ophthalmic device comprising a sensor in accordance with the present disclosure. The ophthalmic device 400 comprises an optic zone 402 and a peripheral zone 404. The optic zone 402 may function to provide one or more of vision correction, vision enhancement, other vision-related functionality, mechanical support, or even a void to permit clear vision. In accordance with the present disclosure, the optic zone 402 may comprise a variable optic element configured to provide enhanced vision at near and distant ranges based on signals sensed from the ciliary muscle. The variable-optic element may comprise any suitable device for changing the focal length of the lens or the refractive power of the lens based upon activation signals from the sensing system described herein. For example, the variable optic element may be as simple as a piece of optical grade plastic incorporated into the lens with the ability to have its spherical curvature changed. The peripheral zone 404 comprises one or more of electrical circuits 406, a power source 408, electrical interconnects 410, mechanical support, as well as other functional elements.

The electrical circuits 406 may comprise one or more integrated circuit die, printed electronic circuits, electrical interconnects, and/or any other suitable devices, including the sensing circuitry described herein. The power source 408 may comprise one or more of battery, energy harvesting, and or any other suitable energy storage or generation devices. It is readily apparent to the skilled artisan that FIG. 4 only represents one exemplary embodiment of an electronic ophthalmic lens and other geometrical arrangements beyond those illustrated may be utilized to optimize area, volume, functionality, runtime, shelf life as well as other design parameters. It is important to note that with any type of variable optic, the fail-safe is distance vision. For example, if power were to be lost or if the electronics fail, the wearer is left with an optic that allows for distance vision.

Figure 5A:
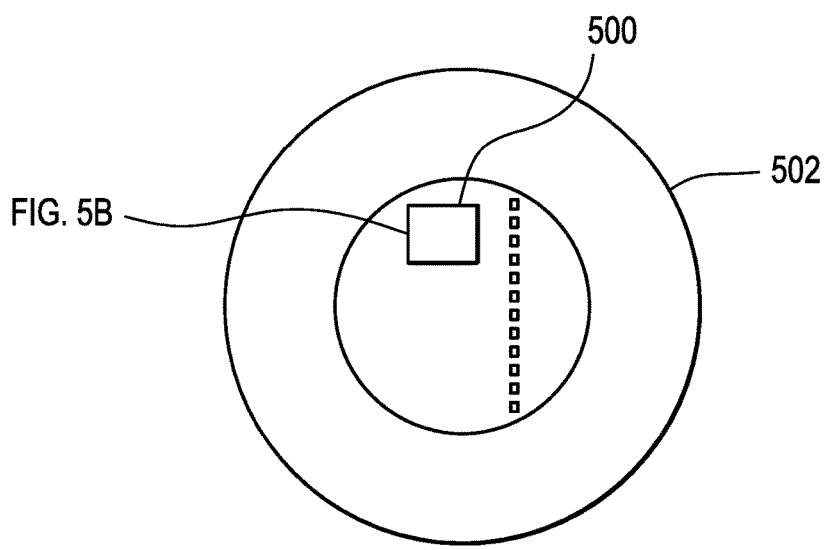
FIG. 5A is a diagrammatic representation of an exemplary electronic system incorporated into an ophthalmic device in accordance with the present disclosure.
Figure 5B:
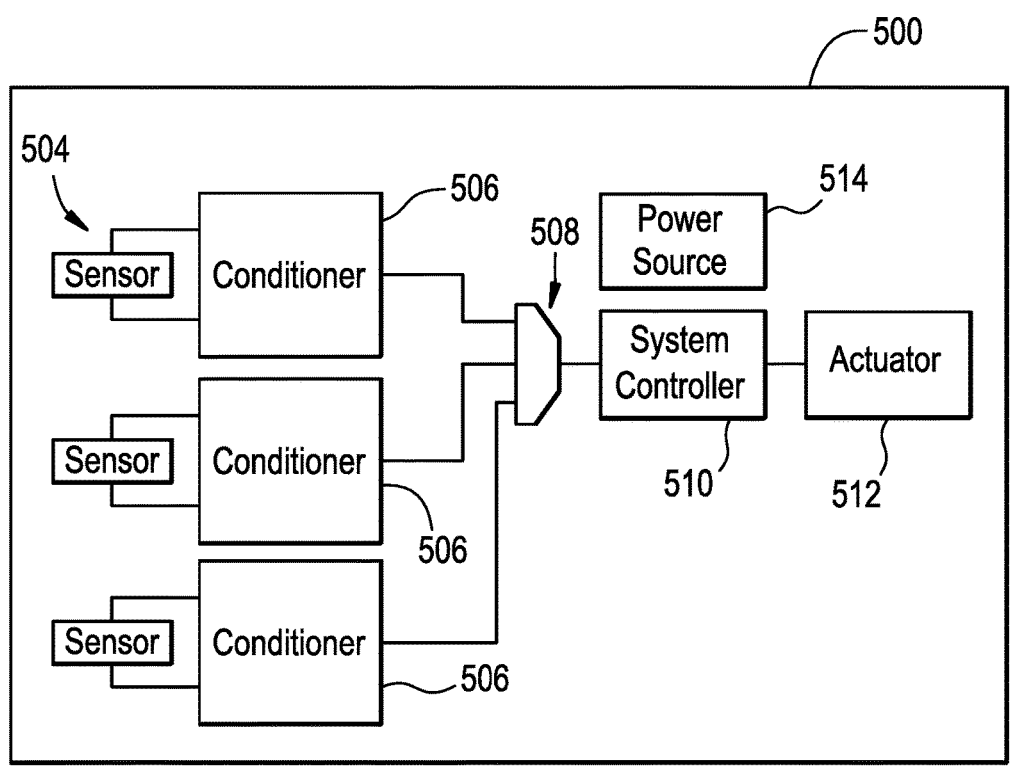
FIG. 5B is an enlarged view of the exemplary electronic system of FIG. 5A
Figure 6:
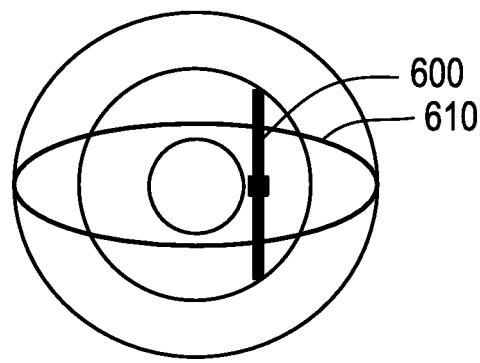
FIG. 6 illustrates a schematic diagram of an exemplary integrator in accordance with some embodiments of the present disclosure.
Figure 7:
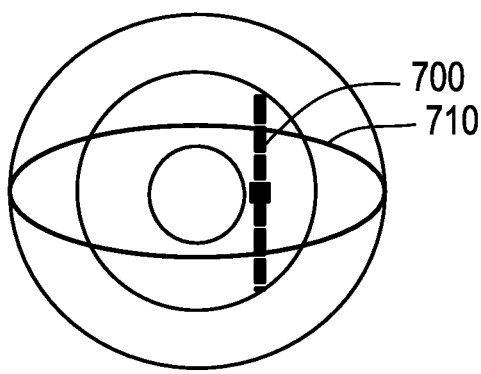
FIG. 7 illustrates a schematic diagram of an exemplary integrator in accordance with some embodiments of the present disclosure.
Figure 8:
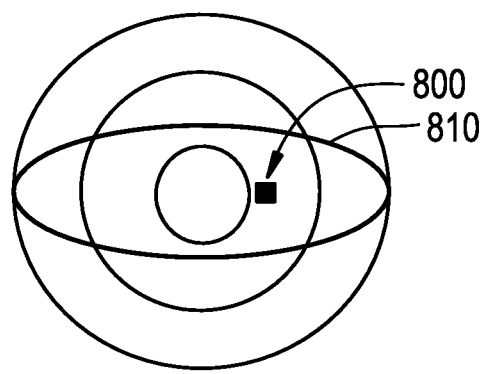
FIG. 8 illustrates a schematic diagram of an exemplary out-of-bounds circuit in accordance with some embodiments of the present disclosure.

FIGS. 5A and 5B illustrate an alternate exemplary detection system 500 incorporated into an ophthalmic device 502 such as a contact lens. FIG. 5A shows the system 500 on the device 502 and FIG. 5B shows an exemplary schematic view of the system 500. In this exemplary embodiment, vibration sensors 504 may be used to sense a displacement at and/or adjacent an eye of the user of the ophthalmic device 502. As an example, the vibration sensors 504 may be configured to detect a displacement that may be affected by a configuration of the ciliary muscle of the user. One or more of the vibration sensors 504 may be configured as linear sensor 600 (FIG. 6), a segmented sensor 700 (FIG. 7), and/or an integrating sensor 800 (FIG. 8) configured to integrate a response over a sensor area. In the various configurations illustrated in FIGS. 6-8, the sensors 600, 700, 800 may be configured to sense a vibration due at least in part to a configuration of the ciliary muscle.

Returning to FIGS. 5A and 5B, sensor conditioners 506 create an output signal indicative of a measurement of one or more sensors 504 in communication with a respective one or more of the sensor conditioners 506. For example, the sensor conditioners may amplify and or filter a signal received from a respective sensor 504. The output of the sensor conditioners 506 may be combined with a multiplexer 508 to reduce downstream circuitry.

In certain embodiments, downstream circuitry may include a system controller 510, which may comprise an analog-to-digital converter (ADC) that may be used to convert a continuous, analog signal into a sampled, digital signal appropriate for further signal processing. For example, the ADC may convert an analog signal into a digital signal that may be useable by subsequent or downstream circuits, such as a digital signal processing system or microprocessor, which may be part of the system controller 510 circuit. A digital signal processing system or digital signal processor may be utilized for digital signal processing, including one or more of filtering, processing, detecting, and otherwise manipulating/processing sampled data. The digital signal processor may be preprogrammed with various displacement signatures. As an example, a data store of vibration (e.g., displacement) measurements or signatures may be mapped to particular configurations of the ciliary muscle and/or other conditions relating to the eye. As such, when vibration measurements matching or near a particular signature are detected, the associated ciliary muscle characteristic or configuration may be extrapolated. Although reference is made to the ciliary muscle configuration, other conditions relating to the eye may be extrapolated such as gaze and/or accommodation. The digital signal processor also comprises associated memory. The digital signal processor may be implemented utilizing analog circuitry, digital circuitry, software, and/or preferably a combination thereof.

The system controller 510 receives inputs from the sensor conditioner 506 via a multiplexor 508, for example, by activating each sensor 504 in order and recording the values. It may then compare measured values to pre-programmed patterns and historical samples to determine a configuration or characteristic of the ciliary muscle. It may then activate a function in an actuator 512, for example, causing a variable-focus lens to change to a closer focal distance. The vibration sensors 504 may be laid out in a physical pattern similar to that previously described and shown in references to FIGS. 1-2 and 6-9, but would be optimized for detecting characteristics and/or changes in configurations of the ciliary muscle. The sensors 504, and/or the whole electronic system, may be encapsulated and insulated from the saline contact lens environment. Various configurations of the sensors 504 may facilitate optimal sensing conditions as the ophthalmic device 502 shifts or rotates.

A power source 514 supplies power for numerous components comprising the lid position sensor system 500. The power source 514 may also be utilized to supply power to other devices on the contact lens. The power may be supplied from a battery, energy harvester, or other suitable means as is known to one of ordinary skill in the art. Essentially, any type of power source 514 may be utilized to provide reliable power for all other components of the system. A vibration sensor array pattern, processed from analog to digital, may enable activation of the system controller 510 or a portion of the system controller 510. Furthermore, the system controller 510 may control other aspects of a powered contact lens depending on input from the multiplexor 508, for example, changing the focus or refractive power of an electronically controlled lens through the actuator 512.

In one exemplary embodiment, the electronics and electronic interconnections are made in the peripheral zone of a contact lens rather than in the optic zone. In accordance with an alternate exemplary embodiment, it is important to note that the positioning of the electronics need not be limited to the peripheral zone of the contact lens. All of the electronic components described herein may be fabricated utilizing thin film technology and/or transparent materials. If these technologies are utilized, the electronic components may be placed in any suitable location as long as they are compatible with the optics. The activities of the digital signal processing block and system controller (system controller 510 in FIG. 5B) depend on the available sensor inputs, the environment, and user reactions. The inputs, reactions, and decision thresholds may be determined from one or more of ophthalmic research, preprogramming, training, and adaptive/learning algorithms. For example, the general characteristics of ciliary muscle configuration may be well-documented in literature, applicable to a broad population of users, and pre-programmed into system controller. However, an individual's deviations from the general expected response may be recorded in a training session or part of an adaptive/learning algorithm which continues to refine the response in operation of the electronic ophthalmic device. In one exemplary embodiment, the user may train the device by activating a handheld fob or user device, such as a smartphone, which communicates with the device, when the user desires near focus. A learning algorithm in the device may then reference sensor inputs in memory before and after the fob signal to refine internal decision algorithms. This training period could last for one day, after which the device would operate autonomously with only sensor inputs and not require the fob.

Figure 9:
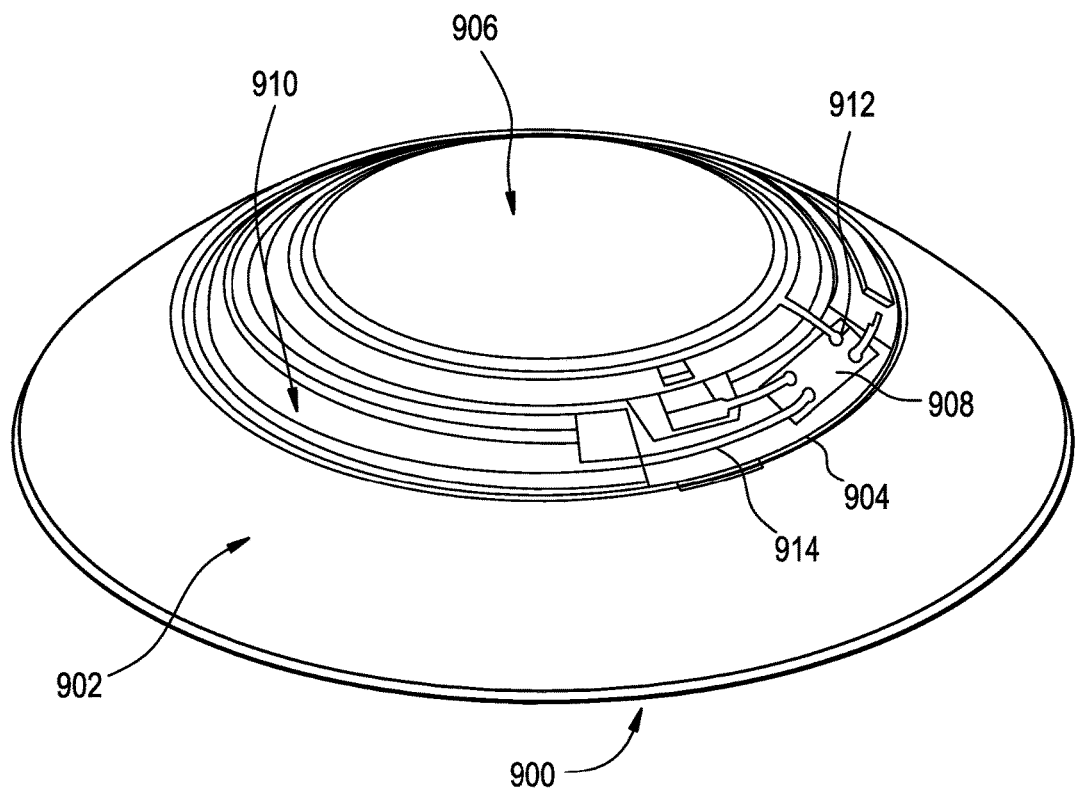
FIG. 9 is a diagrammatic representation of an exemplary powered or electronic ophthalmic device in accordance with the present disclosure.

FIG. 9 is a diagrammatic representation of an exemplary electronic insert, including a combined blink detection and communication system, positioned in a powered or electronic ophthalmic device in accordance with the present disclosure. As shown, a contact lens 900 comprises a soft plastic portion 902 which comprises an electronic insert 904. This insert 904 includes a lens 906 which is activated by the electronics, for example, focusing near or far depending on activation. Integrated circuit 908 mounts onto the insert 904 and connects to batteries 910, lens 906, and other components as necessary for the system. The integrated circuit 908 includes a sensor 912 and associated signal path circuits. The sensor 912 may comprise any sensor configuration such as those described herein. The sensor 912 may also be implemented as a separate device mounted on the insert 904 and connected with wiring traces 914.

Figure 10:
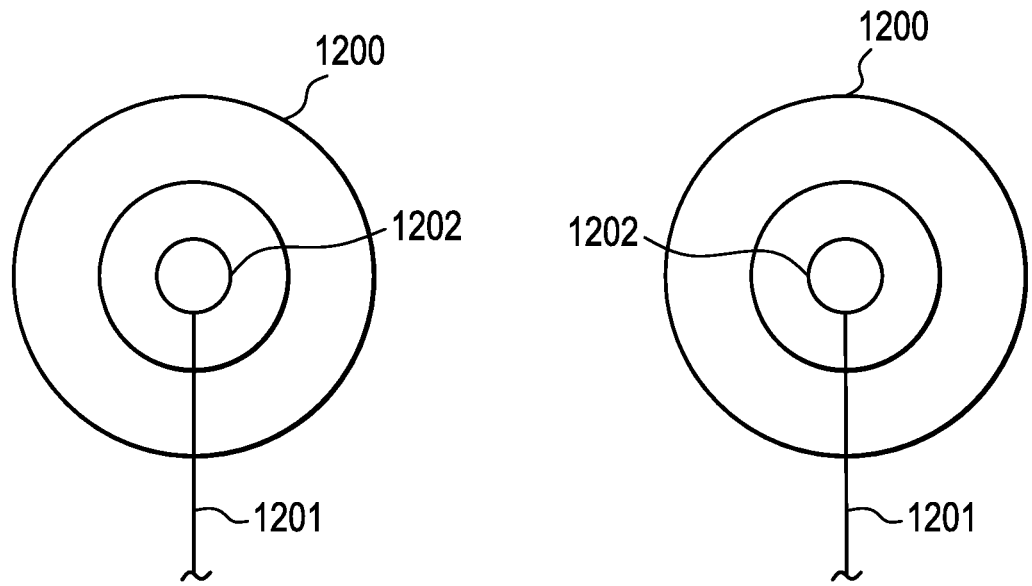
FIG. 10 is a diagrammatic, front perspective representation of the eyes of an individual gazing at a distant object.
Figure 11:
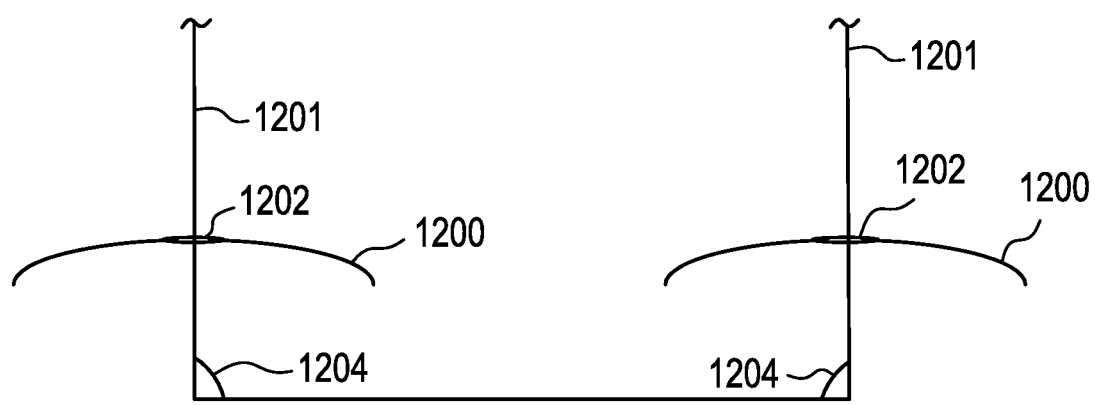
FIG. 11 is a diagrammatic, top perspective representation of the eyes of FIG. 10.

FIGS. 10 and 11 illustrate different views of the two eyes 1200 of an individual who is gazing at a distant object which requires far focus, for example, driving a car, instead of near focus, for example, reading a book. FIG. 10 illustrates a front perspective of the eyes 1200, whereas FIG. 11 illustrates a top perspective of the eyes 1200. While gazing at a distant object, not illustrated, the pupils 1202 are centered and track together. Lines 1201 between the pupils 1202 and the object under observation are parallel as is shown by angles 1204 both being ninety (90) degrees. This is because the distance between the two eyes 1200 on any individual is much less than the distance from the eyes 1200 to the object under observation. As an individual tracks the movement of a distant object, although the eyes 1200 move, the angles 1204 remain very close to ninety (90) degrees, again because the distance between the two eyes 1200 is much less than the distance from the eyes 1200 to the object under observation. During such movement muscles controlling the eye may contract and relax, thereby generating vibration. Additionally or alternatively, as the gaze of the eye changes, the accommodation of the eye may be controlled by contraction and/or relaxation of the ciliary muscle, thereby generating vibrations. Even after a muscle is contract acted, a residual vibration or quiver may be detectable. As such, measurements of these vibrations at known gaze and accommodation may be later used to compare and match unknown vibration signatures to the known set of values. Moreover, vibration signatures of static eye states or transitions between states may be learned and applied to subsequent measurements to extrapolate characteristics relating to the eye.

Figure 12:
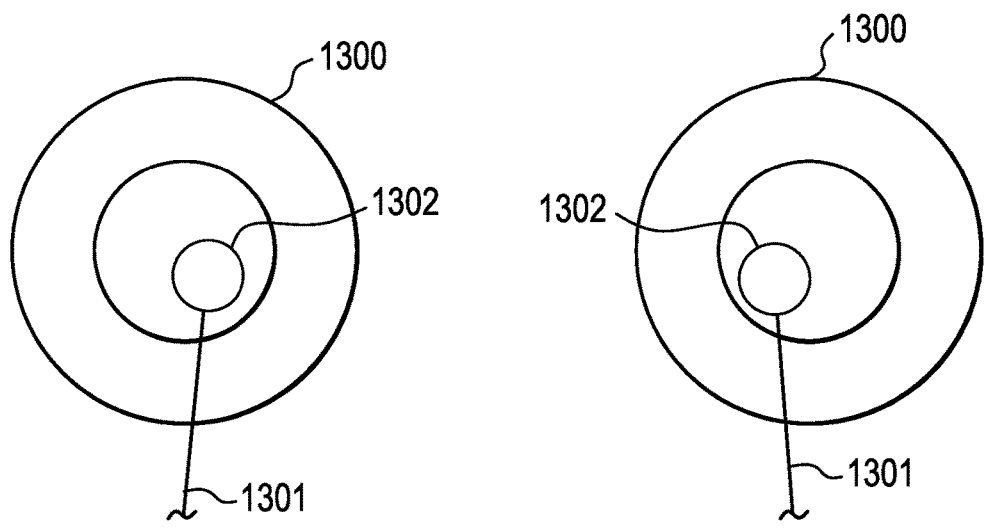
FIG. 12 is a diagrammatic, front perspective representation of the eyes of an individual gazing at a near object.
Figure 13:
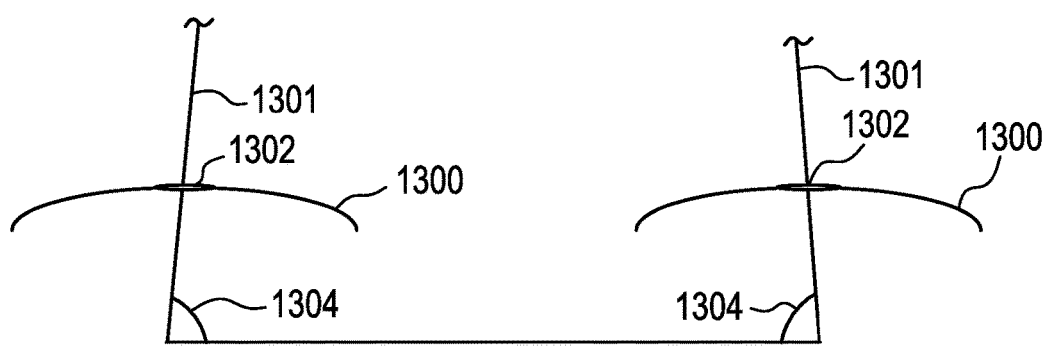
FIG. 13 is a diagrammatic, top perspective representation of the eyes of FIG. 12.

FIGS. 12 and 13 illustrate a pair of eyes 1300 substantially similar to those illustrated in FIGS. 10 and 11, with the exception that in this example the object under observation, not illustrated, is close or near rather than distant. Since the distance between the eyes 1300 is now appreciable relative to the distance from the eyes 1300 to the object under observation, the eyes 1300 converge to keep the object under observation within the field of view. As illustrated, via exaggeration, pupils 1302 converge and move closer together. Lines 1301 drawn between the pupils and the object under observation are no longer parallel, and the angles 1304 are less than ninety (90) degrees. This phenomena may be easily observed by having a subject first focus on his or her finger at an approximate distance of two (2) feet with his or her arm fully extended. As the subject brings his or her finger closer, his or her eyes will converge towards his or her nose becoming "cross-eyed." As with the gaze and accommodation states discussed in FIG. 10-11, the states observed in FIGS. 12-13 may be correlated to vibration/displacement signatures and may be used to extrapolate subsequent characteristics from displacement measurements. Additional gaze and accommodation states may be correlated with displacement signatures such as those illustrated in FIGS. 14-18.

Figure 14:
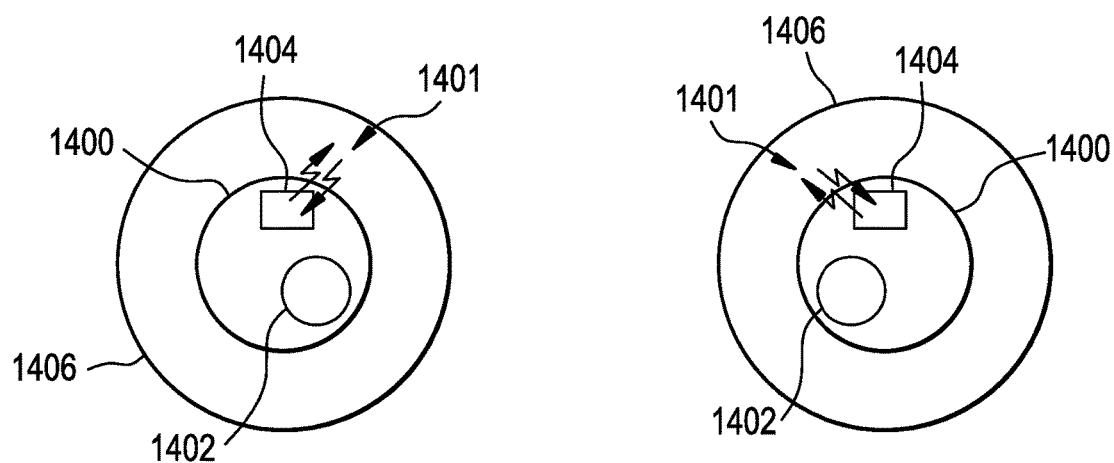
FIG. 14 is a diagrammatic representation of two exemplary pupil position and convergence sensors having a communication channel for synchronizing operation between two eyes in accordance with the present disclosure.

FIG. 14 illustrates a system by which the convergence described with respect to FIGS. 10-13 may be sensed and communicated between a pair of contact lenses 1400. Pupils 1402 are illustrated converged for near object viewing. Pupil position and convergence detection systems 1404 incorporated within contact lenses 1400 that are positioned on eyes 1406 track the position of the pupils 1402 and/or the contact lenses 1400, for example, with reverse-facing photodetectors to observe the pupils 1402 or with accelerometers to track movement of the eyes 1406 and hence the pupils 1402. The pupil position and convergence detector systems 1404 may comprise several components forming a more complex system, for example a 3-axis accelerometer, signal conditioning circuitry, a controller, memory, power supply, and a transceiver as is described in detail subsequently. Communication channel 1401 between the two contact lenses 1400 allows the pupil position and convergence detection systems 1404 to synchronize on pupil position. Communication may also take place with an external device, for example, spectacle glasses or a smartphone. Communication between the contact lenses 1400 is important to detect convergence. For example, without knowing the position of both pupils 1402, simply gazing down to the left may be detected as convergence by the right eye since the pupil 1402 has similar movement for both actions. However, if the right pupil is detected moving down to the left while the pupil of the left eye is detected moving down to the right, convergence may be construed. Communication between the two contact lenses 1400 may take the form of absolute or relative position, or may simply be a "convergence suspected" signal if the eye moves in the expected direction of convergence. In this case, if a given contact lens detects convergence itself and receives a convergence indication from the adjacent contact lens, it may activate a change in stage, for example, switching a variable-focus or variable power optic equipped contact lens to the near distance state to support reading. Other information useful for determining the desire to accommodate (focus near), for example, vibration and ciliary muscle activity, may also be transmitted over the communication channel 1401 if the contact lenses are so equipped. It should also be appreciated that communication over the channel 1401 could comprise other signals sensed, detected, or determined by each lens 1406 and 15 used for a variety of purposes, including vision correction, vision enhancement, entertainment, and novelty.

In accordance with one exemplary embodiment, a digital communication system comprises a number of elements which when implemented, may take on any number of forms. The digital communication system generally comprises an information source, a source encoder, a channel encoder, a digital modulator, a channel, a digital demodulator, a channel decoder and a source decoder. The information source may comprise any device that generates information and/or data that is required by another device or system. The source may be analog or digital. If the source is analog, its output is converted into a digital signal comprising a binary string. The source encoder implements a process of efficiently converting the signal from the source into a sequence of binary digits. The information from the source encoder is then passed into a channel encoder where redundancy is introduced into the binary information sequence. This redundancy may be utilized at the receiver to overcome the effects of noise, interference and the like encountered on the channel. The binary sequence is then passed to a digital modulator which in turn converts the sequence into analog electrical signals for transmission over the channel. Essentially, the digital modulator maps the binary sequences into signal waveforms or symbols. Each symbol may represent the value of one or more bits. The digital modulator may modulate a phase, frequency or amplitude of a high frequency carrier signal appropriate for transmission over or through the channel. The channel is the medium through which the waveforms travel, and the channel may introduce interference or other corruption of the waveforms. In the case of the wireless communication system, the channel is the atmosphere. The digital demodulator receives the channel-corrupted waveform, processes it and reduces the waveform to a sequence of numbers that represent, as nearly as possible, the transmitted data symbols. The channel decoder reconstructs the original information sequence from knowledge of the code utilized by the channel encoder and the redundancy in the received data. The source decoder decodes the sequence from knowledge of the encoding algorithm, wherein the output thereof is representative of the source information signal. It is important to note that the above described elements may be realized in hardware, in software or in a combination of hardware and software. In addition, the communication channel may comprise any type of channel, including wired and wireless. In wireless, the channel may be configured for high frequency electromagnetic signals, low frequency electromagnetic signals, visible light signals and infrared light signals.

Figure 15A:
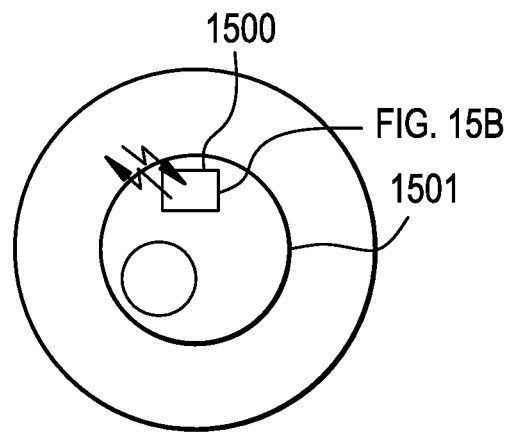
FIG. 15A is a diagrammatic representation of an exemplary pupil position and convergence detection system incorporated into a contact lens in accordance with the present disclosure.
Figure 15B:
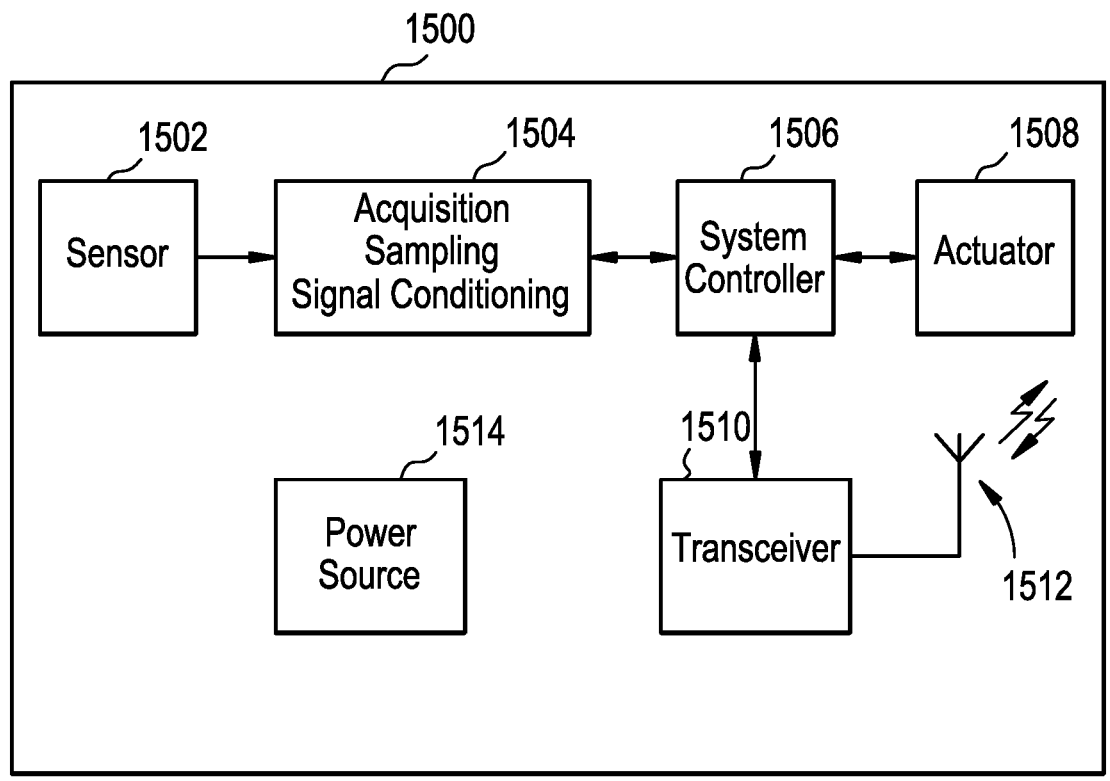
FIG. 15B is an enlarged view of the exemplary pupil position and convergence detection system of FIG. 15A.

FIGS. 15A and 15B are diagrammatic representations of an exemplary pupil position and convergence detection system 1500 for control of one or more aspects of a powered ophthalmic lens. Sensor 1502 detects the movement and/or position of the pupil or, more generally, the eye. The sensor 1502 may be implemented as a multi-axis accelerometer on a contact lens 1501. Such sensors 1502 may be used in conjunction with the vibration sensors described herein. With the contact lens 1501 being affixed to the eye and generally moving with the eye, an accelerometer on the contact lens 1501 may track eye movement. The sensor 1502 may also be implemented as a rear-facing camera or sensor which detects changes in images, patterns, or contrast to track eye movement. Alternately, the sensor 1502 may comprise neuromuscular sensors to detect nerve and/or muscle activity which moves the eye in the socket. There are six muscles attached to each eye globe which provide each eye with a full range of movement and each muscle has its own unique action or actions. These six muscles are innervated by one of the three cranial nerves. It is important to note that any suitable device may be utilized as the sensor 1502, and more than a single sensor 1502 may be utilized. The output of the sensor 1502 is acquired, sampled, and conditioned by signal processor 1504. The signal processor 1504 may include any number of devices including an amplifier, a transimpedance amplifier, an analog-to-digital converter, a filter, a digital signal processor, and related circuitry to receive data from the sensor 1502 and generate output in a suitable format for the remainder of the components of the system 1500. The signal processor 1504 may be implemented utilizing analog circuitry, digital circuitry, software, and/or preferably a combination thereof. It should be appreciated that the signal processor 1504 is co-designed with the sensor 1502 utilizing methods that are known in the relevant art, for example, circuitry for acquisition and conditioning of an accelerometer are different than the circuitry for a muscle activity sensor or optical pupil tracker. The output of the signal processor 1504 is preferentially a sampled digital stream and may include absolute or relative position, movement, detected gaze in agreement with convergence, or other data. System controller 1506 receives input from the signal processor 1504 and uses this information, in conjunction with other inputs, to control the electronic contact lens 1501. For example, the system controller 1506 may output a signal to an actuator 1508 that controls a variable power optic in the contact lens 1501. If, for example, the contact lens 1501 is currently in a far focus state and the sensor 1502 detects convergence, the system controller 1506 may command the actuator 1508 to change to a near focus state. System controller 1506 may both trigger the activity of sensor 1502 and the signal processor 1504 while receiving output from them. A transceiver 1510 receives and/or transmits communication through antenna 1502. This communication may come from an adjacent contact lens, spectacle lenses, or other devices. The transceiver 1510 may be configured for two way communication with the system controller 1506. Transceiver 1510 may contain filtering, amplification, detection, and processing circuitry as is common in transceivers. The specific details of the transceiver 1510 are tailored for an electronic or powered contact lens, for example the communication may be at the appropriate frequency, amplitude, and format for reliable communication between eyes, low power consumption, and to meet regulatory requirements. Transceiver 1510 and antenna 1512 may work in the radio frequency (RF) bands, for example 2.4 GHz, or may use light for communication. Information received from transceiver 1510 is input to the system controller 1506, for example, information from an adjacent lens which indicates convergence or divergence. System controller 1506 uses input data from the signal processor 1504 and/or transceiver 1510 to decide if a change in system state is required. The system controller 1506 may also transmit data to the transceiver 1510, which then transmits data over the communication link via antenna 1512. The system controller 1506 may be implemented as a state machine, on a field-programmable gate array, in a microcontroller, or in any other suitable device. Power for the system 1500 and components described herein is supplied by a power source 1514, which may include a battery, energy harvester, or similar device as is known to one of ordinary skill in the art. The power source 1514 may also be utilized to supply power to other devices on the contact lens 1501. The exemplary pupil position and convergence detection system 1500 of the present disclosure is incorporated and/or otherwise encapsulated and insulated from the saline contact lens 1501 environment.

Figure 16:
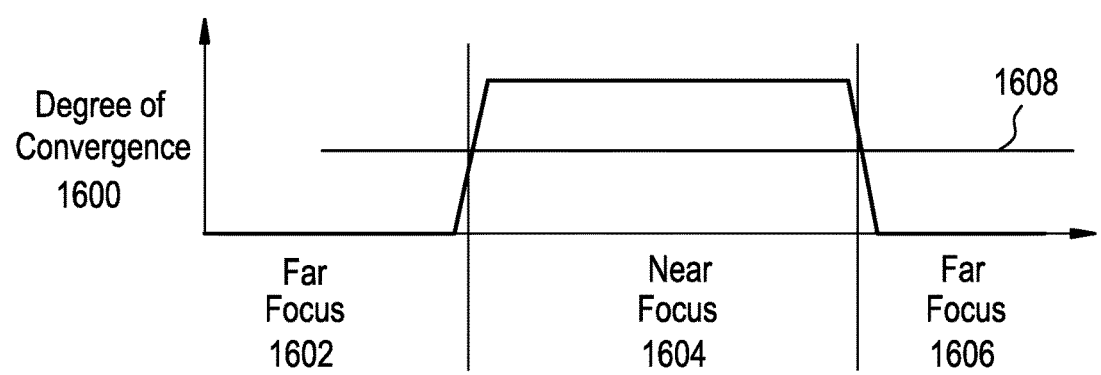
FIG. 16 is a diagrammatic representation of an exemplary plot of the correlation between pupil convergence and focal distance.

FIG. 16 illustrates an exemplary, simplified correlation between convergence 1600 and focal length states 1602, 1604, and 1606 as is commonly documented in the ophthalmic literature. When in the far focus state 1602 and 1606, as described with respect to FIGS. 12A and 12B, the degree of convergence is low. When in the near focus state 1604, as described with respect to FIGS. 13A and 13B, the degree of convergence is high. A threshold 1608 may be set in the system controller (element 1506 of FIG. 15) to change the state of the electronic ophthalmic lens, for example, focusing a variable optic with add power when the threshold is passed going positive then focusing the variable optic with no add power when the threshold is passed going negative.

Figure 17A:
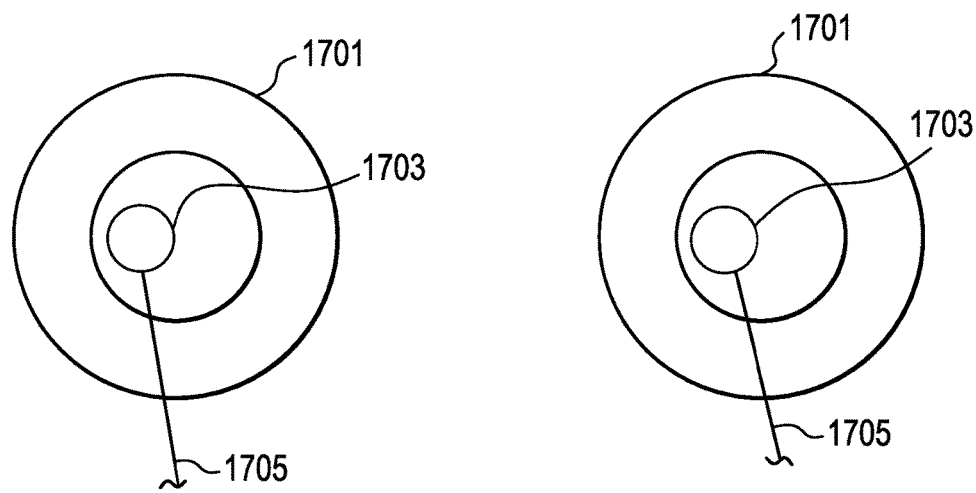
FIG. 17A is a diagrammatic, front perspective representation of the eyes of an individual gazing to the right.
Figure 17B:
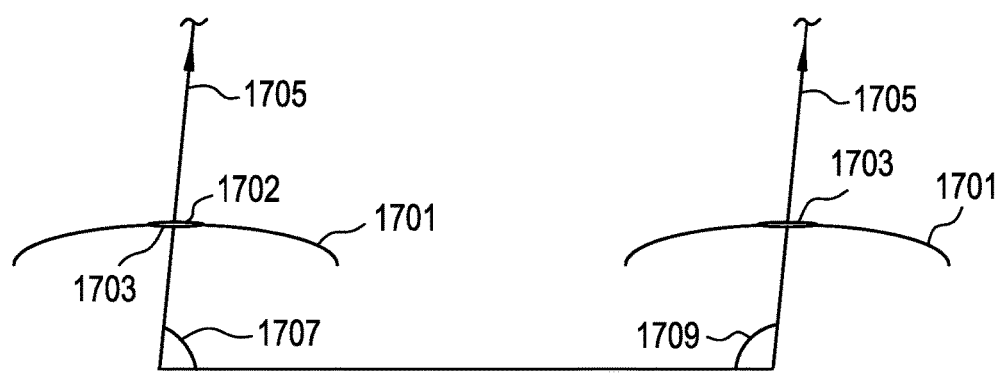
FIG. 17B is a diagrammatic, top perspective representation of the eyes of FIG. 17A.

FIGS. 17A and 17B illustrate a pair of eyes 1701 substantially similar to those 25 illustrated in FIGS. 12A and 12B, with the exception that in this example the object under observation, not illustrated, is to the right of the user. FIG. 17A illustrates a front perspective of the eyes 1701, whereas FIG. 17B illustrates a top perspective of the eyes 1701. The position to the right is used for illustrative purposes, but it should be appreciated that the object under observation could be at any visible point in three dimension space with the corresponding changes in eye gaze. As illustrated, via exaggeration, pupils 1703 both face toward the right. Lines 1705 drawn between the pupils 1703 and the object under observation are almost parallel since the object is illustrated to be much farther from the eyes 1701 than the distance between the eyes 1701. Angle 1707 is less than ninety (90) degrees whereas angle 1709 is greater than ninety (90) degrees. These angles are in contrast to previous figures where the angles were either both ninety (90) degrees, when gazing straight ahead at a distant object, or both less than ninety degrees, when gazing straight ahead at a nearby object. As is illustrated in two dimensions, the angle may be used to determine gaze position or, more generally, samples of eye movement may be utilized to determine absolute and relative position and movement of eye gaze.

Figure 18:
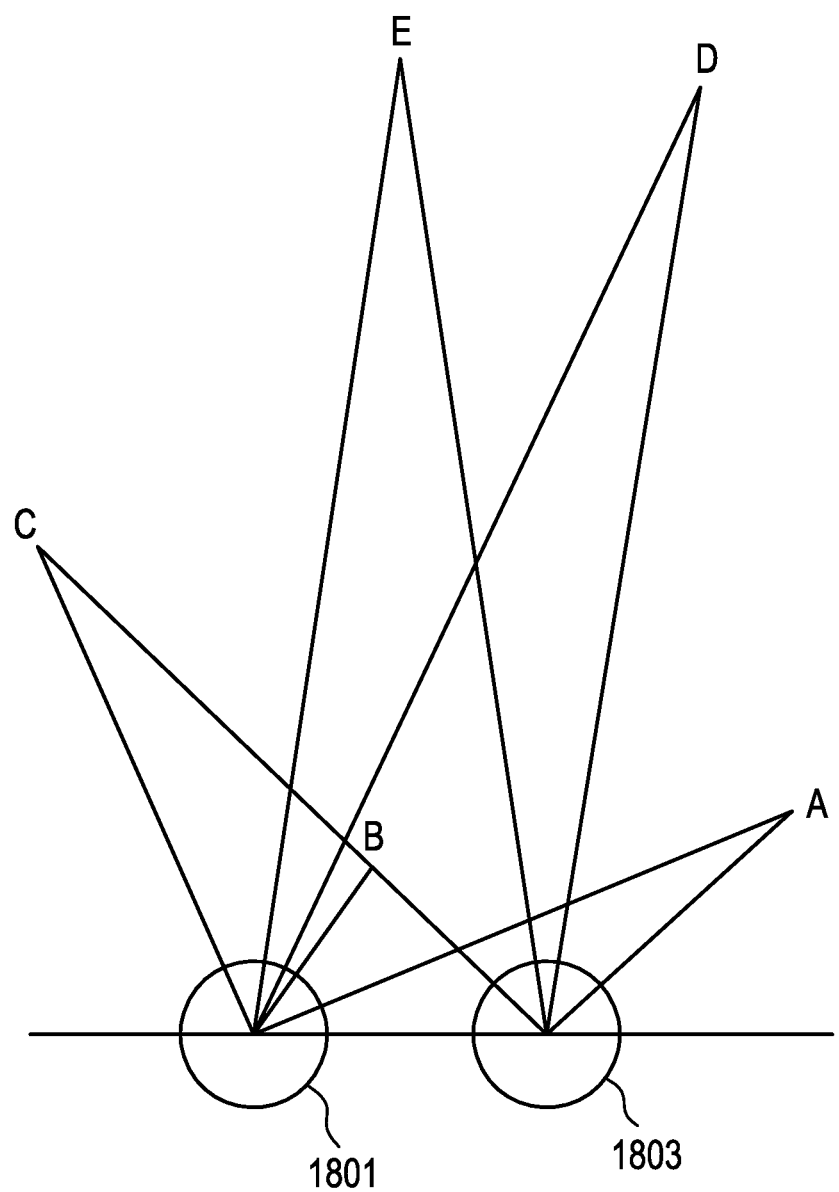
FIG. 18 is a diagrammatic representation of the geometry associated with various gaze directions in two dimensions in accordance with the present disclosure.

FIG. 18 illustrates the geometric systems associated with various gaze directions. FIG. 18 is a top view. Eyes 1801 and 1803 are shown gazing upon various targets labeled A, B, C, D, and E. A line connects each eye 1801 and 1803 to each target. A triangle is formed by each of the two lines connecting the eyes 1801 and 1803 with a given target in addition to a line connecting both eyes 1801 and 1803. As may be seen in the illustration, the angles between the direction of gaze in each eye 1801 and 1803 and the line between the two eyes 1801 and 1803 varies for each target. These angles may be measured by the sensor system, determined from indirect sensor measurements, or may only be shown for illustrative purposes. Although shown in two dimensional space for simplicity of illustration, it should be apparent that gaze occurs in three-dimensional space with the corresponding addition of an additional axis. Targets A and B are shown relatively near to the eyes 1801 and 1803, for example, to be read with near-focus accommodation. Target A is to the right of both eyes 1801 and 1803, hence both eyes 1801 and 1803 are pointing right. Measuring the angle formed anticlockwise between the horizontal axis, illustrated collinear with the line connecting the two eyes 1801 and 1803, and direction of gaze, both angles are acute for target A. Now referring to target B the eyes 1801 and 1803 are converged on a target in front of and between both eyes 1801 and 1803. Hence the angle, previously defined as anticlockwise from the horizontal axis and the direction of gaze, is obtuse for the right eye 1803 and acute for the left eye 1801. A suitable sensor system will differentiate the positional difference between targets A and B with suitable accuracy for the application of concern. Target C is shown at intermediate distance for the special case of the right eye 1803 having the same direction of gaze and angle as target B. The gaze direction varies between targets B and C allowing a gaze direction determination system using inputs from both eyes 1801 and 1803 to determine the direction of gaze. Further, a case could be illustrated where another target F lies above target B in three-dimensional space. In such an example, projected into the two-dimensional illustration shown in FIG. 18, the angles from the horizontal axis would be identical to those illustrated for target B. However, the angles normal to the page extending in three-dimensional space would not be equal between the targets. Finally, targets D and E are shown as distant objects. These examples illustrate that as the object under gaze is farther away, the angular difference at the eyes 1801 and 1803 between distant points becomes smaller. A suitable system for detecting gaze direction would have sufficient accuracy to 15 differentiate between small, distant objects.

The direction of gaze may be determined by any number of suitable devices, for example, with reverse-facing photodetectors to observe the pupils or with accelerometers to tack the movement of the eyes. Neuromuscular sensors may also be utilized. Such sensors may be used in conjunction with vibration sensors to generate displacement signatures. By monitoring the six muscles that control eye movement, the precise direction of gaze may be determined. A memory element to store prior position and/or acceleration may be required in addition to a position computation system considering present and past sensor inputs. In addition, the system illustrated in FIGS. 15A and 15B are equally applicable to the gaze and tracking system of the present disclosure.

The system is preferably programmed to account for gazing geometries in three dimensional space. It is known in the art of optometry that the eyes do not remain completely stable when gazing at a stationary object. Rather, the eyes quickly move back and forth. A suitable system for detecting gaze position would include the necessary filtering and/or compensation to account for visual physiology. For example, such a system may include a low-pass filter or an algorithm specially tuned to a user's natural eye behaviors.

In one exemplary embodiment, the electronics and electronic interconnections are made in the peripheral zone of a contact lens rather than in the optic zone. In accordance with an alternate exemplary embodiment, it is important to note that the positioning of the electronics need not be limited to the peripheral zone of the contact lens. All of the electronic components described herein may be fabricated utilizing thin film technology and/or transparent materials. If these technologies are utilized, the electronic components may be placed in any suitable location as long as they are compatible with the optics.

The activities of the acquisition sampling signal processing block and system controller (1504 and 1506 in FIG. 15B, respectively) depend on the available sensor inputs, the environment, and user reactions. The inputs, reactions, and decision thresholds may be determined from one or more of ophthalmic research, preprogramming, training, and adaptive/learning algorithms. For example, the general characteristics of eye movement may be well-documented in literature, applicable to a broad population of users, and pre-programmed into system controller. However, an individual's deviations from the general expected response may be recorded in a training session or part of an adaptive/learning algorithm which continues to refine the response in operation of the electronic ophthalmic device. In one exemplary embodiment, the user may train the device by activating a handheld fob, which communicates with the device, when the user desires near focus. A learning algorithm in the device may then reference sensor inputs in memory before and after the fob signal to refine internal decision algorithms. This training period could last for one day, after which the device would operate autonomously with only sensor inputs and not require the fob. An intraocular lens or IOL is a lens that is implanted in the eye and replaces the crystalline lens. It may be utilized for individuals with cataracts or simply to treat various refractive errors. An IOL typically comprises a small plastic lens with plastic side struts called haptics to hold the lens in position within the capsular bag in the eye. Any of the electronics and/or components described herein may be incorporated into IOLs in a manner similar to that of contact lenses.

Although shown and described in what is believed to be the most practical and preferred embodiments, it is apparent that departures from specific designs and methods described and shown will suggest themselves to those skilled in the art and may be used without departing from the spirit and scope of the disclosure. The present disclosure is not restricted to the particular constructions described and illustrated, but should be constructed to cohere with all modifications that may fall within the scope of the appended claims.

What is claimed is:

1. An ophthalmic device comprising:
a variable-optic element incorporated into the ophthalmic lens, the variable-optic element being configured to change a refractive power of the ophthalmic lens;
a vibration sensor disposed in the ophthalmic lens, the vibration sensor configured to detect a vibration caused at least in part by ciliary muscle movement associated with the process of accommodation, the vibration sensor further configured to provide an output, wherein the variable-optic element is configured to be controlled based at least on the output;
a computer readable storage medium onto which are stored a plurality of preprogrammed displacement signatures each being indicative of an eye gaze, eye convergence, accommodation, or a combination thereof; and
a processor configured to receive the output and to determine a characteristic of the output indicative of the ciliary muscle movement, and to compare the characteristic with at least one of the preprogrammed displacement signatures and comparative data from an eye, wherein the comparative data relates to eye movement and includes at least one or more of maximum velocities of saccades, peak velocity, duration of saccades, and first peak acceleration.

2. The ophthalmic device according to claim 1, wherein the ophthalmic lens comprises a contact lens.

3. The ophthalmic device according to claim 2, wherein the contact lens comprises a soft or hybrid contact lens.

4. The ophthalmic device according to claim 1, wherein the vibration sensor comprises one or more contacts configured to make direct contact with a tear film of an eye to detect vibrations produced by the ciliary muscle.

5. The ophthalmic device according to claim 1, wherein the vibration sensor comprises a displacement sensor.

6. The ophthalmic device according to claim 1, further comprising a power source in electrical communication with one or more of the vibration sensor and the variable-optic element.

7. The ophthalmic device according to claim 6, wherein the power source comprises a battery.

8. The ophthalmic device according to claim 1, further comprising a controller configured to receive the output of the vibration sensor and to control the variable-optic element to at least change the refractive power of the ophthalmic lens.

9. The ophthalmic device according to claim 8, wherein the controller is further configured to isolate a ciliary muscle component from a non-ciliary muscle component of the output of the vibration sensor in the time domain.

10. The ophthalmic device according to claim 9, wherein non-ciliary muscle component comprise signal noise.

11. The ophthalmic device according to claim 8, wherein the controller is further configured to isolate a ciliary muscle component from a non-ciliary muscle component of the output of the vibration sensor in the frequency domain.

12. The ophthalmic device according to claim 11, wherein non-ciliary muscle component comprise signal noise.

13. The ophthalmic device according to claim 1, further comprising an amplifier operatively associated with the vibration sensor.

14. The ophthalmic device according to claim 1, further comprising an analog-to-digital converter operatively associated with the vibration sensor.

15. A sensor system for an ophthalmic device, the sensor system comprising:
a vibration sensor disposed adjacent an eye of a user, the vibration sensor configured to detect a vibration caused at least in part by ciliary muscle movement, the vibration sensor further configured to provide an output;
a computer readable storage medium onto which are stored a plurality of preprogrammed displacement signatures each being indicative of an eye gaze, eye convergence, accommodation, or a combination thereof; and
a processor configured to receive the output and to determine a characteristic of the output indicative of the ciliary muscle movement, and to compare the characteristic with at least one of the preprogrammed displacement signatures and comparative data from an eye, wherein the comparative data relates to eye movement and includes at least one or more of maximum velocities of saccades, peak velocity, duration of saccades, and first peak acceleration.

16. The sensor system according to claim 15, further comprising a power source in electrical communication with one or more of the vibration sensor and the processor.

17. The sensor system according to claim 16, wherein the power source comprises a battery.

18. The sensor system according to claim 15, wherein the characteristic comprises a displacement.

19. The sensor system according to claim 15, wherein the processor is further configured to isolate a ciliary muscle component from a non-ciliary muscle component of the characteristic in the time domain.

20. The sensor system according to claim 19, wherein non-ciliary muscle component comprise signal noise.

21. The sensor system according to claim 15, wherein the processor is further configured to isolate a ciliary muscle component from a non-ciliary muscle component of the characteristic in the frequency domain.

22. The sensor system according to claim 21, wherein non-ciliary muscle component comprise signal noise.

23. The sensor system according to claim 15, further comprising an amplifier and analog-to-digital converter operatively associated with the vibration sensor.

24. The sensor system according to claim 15, further comprising an actuator operatively associated with the processor, wherein the actuator is configured to be controlled based on at least the determined characteristic.

25. The sensor system according to claim 15, wherein the vibration sensor comprises a contact-based sensor having one or more contacts configured to make direct contact with a tear film of the eye to detect vibration produced by at least the ciliary muscle.

26. A method for determining a characteristic of the ciliary muscle of a user of an ophthalmic device, the method comprising:
receiving, via a vibration sensor disposed adjacent an eye of the user, a vibration signal indicative of a vibration caused at least in part by a change in the characteristic of the ciliary muscle;
comparing the vibration signal with at least one preprogrammed displacement signature indicative of an eye gaze, eye convergence, accommodation, or a combination thereof and comparative data from an eye, wherein the comparative data relates to eye movement and includes at least one or more of maximum velocities of saccades, peak velocity, duration of saccades, and first peak acceleration; and
implementing, via a control, a predetermined function associated with the ophthalmic device.

27. The method according to claim 26, wherein the characteristic comprises a spatial configuration of the ciliary muscle.

28. The method according to claim 26, wherein the determining the displacement signature comprises isolating a ciliary muscle component from a non-ciliary muscle component of the characteristic in the time domain.

29. The method according to claim 28, wherein non-ciliary muscle component comprise signal noise.

30. The method according to claim 26, wherein the determining the displacement signature comprises isolating a ciliary muscle component from a non-ciliary muscle component of the characteristic in the frequency domain.

31. The method according to claim 30, wherein non-ciliary muscle component comprise signal noise.

32. The method according to claim 26, wherein the determining the displacement signature comprises comparing the vibration signal to a set of generated signatures and selecting at least one of the set of generated signatures as the displacement signature.

* * * * *